US 7,083,649 B2

(12) United States Patent
Zucherman et al.

(10) Patent No.: US 7,083,649 B2
(45) Date of Patent: Aug. 1, 2006

(54) ARTIFICIAL VERTEBRAL DISK REPLACEMENT IMPLANT WITH TRANSLATING PIVOT POINT

(75) Inventors: James F. Zucherman, San Francisco, CA (US); Ken Y. Hsu, San Francisco, CA (US); Charles J. Winslow, Walnut Creek, CA (US); Scott A. Yerby, Montara, CA (US); Steve Mitchell, Pleasant Hill, CA (US); John Flynn, Concord, CA (US)

(73) Assignee: St. Francis Medical Technologies, Inc., Concord, CA (US)

( * ) Notice: Subject to any disclaimer, the term of this patent is extended or adjusted under 35 U.S.C. 154(b) by 0 days.

(21) Appl. No.: 10/684,669

(22) Filed: Oct. 14, 2003

(65) Prior Publication Data

US 2004/0138749 A1    Jul. 15, 2004

Related U.S. Application Data

(60) Provisional application No. 60/422,039, filed on Oct. 29, 2002.

(51) Int. Cl.
*A61F 2/44* (2006.01)
(52) U.S. Cl. .................. 623/17.11; 623/17.14; 623/17.15
(58) Field of Classification Search .. 623/17.11–17.16; 606/61
See application file for complete search history.

(56) References Cited

U.S. PATENT DOCUMENTS 2,456,806 A    12/1948    Wolffe (Continued)

FOREIGN PATENT DOCUMENTS

CA    2015507    1/1991

(Continued)

OTHER PUBLICATIONS

*Ceramic Interspinous Block (CISB) Assisted Anterior Interbody Fusion*, Haruo Tsuji, Norikazu Hirano, Yoshiharu Katoh, Hiroshi Ohsima, Hirokazu Ishihara, Hisao Matsui,and Yohihiko Hayashi, Journal of Spinal Disorders vol. 3. No. 1, pp. 77-86, c1990 Raven Press, Ltd., New York.
*Instrumentation and Implants for Spinal Surgery*,J. Dabb, Diary of the XVIIIth Scientific Meeting of the PTO Tr/Pamietnik XVIII Zjazdu Naukowego PTO Tr/PZ,WL, Warszawa, Link America Inc., 1971, 665.
*Spinal Stenosis and Neurogenic Claudication*, Richard W. Porter, MD, FRCS, FRCSE, SPINE vol. 21, No. 17, pp. 2046-2052, c1996, Lippincott-Raven Publishers.
*Preliminary Design and Experimental Studies of a Novel Soft Implant for Correcting Sagittal Plan Instability in the Lumbar Spine*, R.J.Minns, BEng, Msc, PhD, DscTech, and W.K. Walsh, FRCS, SPINE vol. 22, No. 16, pp. 1819-1827, c1997, Lippincott-Raven Publishers.

*Primary Examiner*—Pedro Philogene
(74) *Attorney, Agent, or Firm*—Fliesler Meyer LLP

(57) ABSTRACT

An artificial vertebral disk replacement implant is disclosed along with its method of operation and a method of implanting. The implant has first and second plates that each mate with a vertebral body. Each plate has one side for mating with a vertebral body. The first plate has a socket on one side, and the second plate has an elongated ball on one side. The ball of the first plate and the socket of the second plate form a ball-and-socket joint when the two plates are in contact with each other. The implant achieves a range of motion equivalent to a natural range of motion.

35 Claims, 22 Drawing Sheets

U.S. PATENT DOCUMENTS

| | | | |
|---|---|---|---|
| 2,677,369 A | 5/1954 | Knowles | 128/92 |
| 3,648,691 A | 3/1972 | Lumb | 128/92 |
| 3,867,728 A | 2/1975 | Stubstad et al. | |
| 3,875,595 A | 4/1975 | Froning | |
| 4,309,777 A | 1/1982 | Patil | |
| 4,349,921 A | 9/1982 | Kuntz | |
| 4,369,769 A | 1/1983 | Edwards | |
| 4,401,112 A | 8/1983 | Rezaian | |
| 4,479,491 A | 10/1984 | Martin | |
| 4,501,269 A | 2/1985 | Bagby | |
| 4,553,273 A | 11/1985 | Wu | |
| 4,554,914 A | 11/1985 | Kapp et al. | |
| 4,599,084 A | 7/1986 | Nashef | |
| 4,599,086 A | 7/1986 | Doty | |
| 4,636,217 A | 1/1987 | Ogilvie | |
| 4,657,550 A | 4/1987 | Daher | |
| 4,685,447 A | 8/1987 | Iversen et al. | |
| 4,696,290 A | 9/1987 | Steffee | |
| 4,714,469 A | 12/1987 | Kenna | |
| 4,743,256 A | 5/1988 | Brantigan | |
| 4,759,766 A | 7/1988 | Buttner-Janz et al. | |
| 4,759,769 A | 7/1988 | Hedman et al. | |
| 4,772,287 A | 9/1988 | Ray et al. | |
| 4,790,303 A | 12/1988 | Steffee | |
| 4,834,757 A | 5/1989 | Brantigan | |
| 4,863,477 A | 9/1989 | Monson | |
| 4,874,389 A | 10/1989 | Downey | |
| 4,878,915 A | 11/1989 | Brantigan | |
| 4,904,260 A | 2/1990 | Ray et al. | |
| 4,904,261 A | 2/1990 | Dove et al. | |
| 4,911,718 A | 3/1990 | Lee et al. | |
| 4,932,969 A | 6/1990 | Frey et al. | |
| 4,932,975 A | 6/1990 | Main et al. | |
| 4,936,848 A | 6/1990 | Bagby | |
| 4,946,378 A | 8/1990 | Hirayama et al. | |
| 4,961,740 A | 10/1990 | Ray et al. | |
| 4,969,888 A | 11/1990 | Scholten et al. | |
| 4,997,432 A | 3/1991 | Keller | |
| 5,002,576 A | 3/1991 | Furhmann et al. | |
| 5,011,484 A | 4/1991 | Breard | 606/61 |
| 5,015,247 A | 5/1991 | Michelson | |
| 5,026,373 A | 6/1991 | Ray et al. | |
| 5,035,716 A | 7/1991 | Downey | |
| 5,047,055 A | 9/1991 | Bao et al. | |
| 5,055,104 A | 10/1991 | Ray | |
| 5,059,193 A | 10/1991 | Kuslich | |
| 5,059,194 A | 10/1991 | Michelson | |
| 5,071,437 A | 12/1991 | Steffee | |
| 5,108,438 A | 4/1992 | Stone | |
| 5,108,442 A | 4/1992 | Smith | |
| 5,122,130 A | 6/1992 | Keller | |
| 5,123,926 A | 6/1992 | Pisharodi | |
| 5,167,662 A | 12/1992 | Hayes et al. | |
| 5,171,280 A | 12/1992 | Baumgartner | |
| 5,171,281 A | 12/1992 | Parsons et al. | |
| 5,180,381 A | 1/1993 | Aust et al. | |
| 5,192,326 A | 3/1993 | Bao et al. | |
| 5,192,327 A | 3/1993 | Brantigan | |
| 5,246,458 A | 9/1993 | Graham | |
| 5,258,031 A | 11/1993 | Salib et al. | |
| 5,258,043 A | 11/1993 | Stone | |
| 5,263,953 A | 11/1993 | Bagby | |
| 5,290,312 A | 3/1994 | Kojimoto et al. | |
| 5,306,307 A | 4/1994 | Senter | |
| 5,306,308 A | 4/1994 | Gross et al. | |
| 5,306,309 A | 4/1994 | Wagner et al. | |
| 5,313,962 A | 5/1994 | Obenchain | |
| 5,314,477 A | 5/1994 | Marnay | |
| 5,314,478 A | 5/1994 | Oka et al. | |
| 5,320,644 A | 6/1994 | Baumgartner | |
| 5,336,223 A | 8/1994 | Rogers | |
| 5,350,397 A | 9/1994 | Palermo et al. | |
| 5,352,225 A | 10/1994 | Yuan et al. | |
| 5,354,302 A | 10/1994 | Ko | |
| 5,360,430 A | 11/1994 | Lin | |
| 5,366,508 A | 11/1994 | Brekke | |
| 5,370,693 A | 12/1994 | Kelman et al. | |
| 5,370,697 A | 12/1994 | Baumgartner | |
| 5,375,823 A | 12/1994 | Navas | |
| 5,383,884 A | 1/1995 | Summers | |
| 5,390,683 A | 2/1995 | Pisharodi | |
| 5,395,317 A | 3/1995 | Kambin | |
| 5,395,372 A | 3/1995 | Holt et al. | |
| 5,397,364 A | 3/1995 | Kozak et al. | |
| 5,401,269 A | 3/1995 | Buttner-Janz et al. | |
| 5,415,704 A | 5/1995 | Davidson | |
| 5,423,816 A | 6/1995 | Lin | |
| 5,423,817 A | 6/1995 | Lin | |
| 5,425,772 A | 6/1995 | Brantigan | |
| 5,425,773 A | 6/1995 | Boyd et al. | |
| 5,425,777 A | 6/1995 | Sarkisian et al. | |
| 5,431,658 A | 7/1995 | Moskovich | |
| 5,439,464 A | 8/1995 | Shapiro | |
| 5,443,514 A | 8/1995 | Steffee | |
| 5,443,515 A | 8/1995 | Cohen et al. | |
| 5,445,639 A | 8/1995 | Kuslich et al. | |
| 5,454,812 A | 10/1995 | Lin | |
| 5,456,722 A | 10/1995 | McLeod et al. | |
| 5,458,638 A | 10/1995 | Kuslich et al. | |
| 5,458,641 A | 10/1995 | Ramirez Jimenez | |
| 5,458,642 A | 10/1995 | Beer et al. | |
| 5,458,643 A | 10/1995 | Oka et al. | |
| 5,480,401 A | 1/1996 | Navas | |
| 5,480,442 A | 1/1996 | Bertagnoli | |
| 5,484,437 A | 1/1996 | Michelson | |
| 5,489,307 A | 2/1996 | Kuslich et al. | |
| 5,489,308 A | 2/1996 | Kuslich et al. | |
| 5,496,318 A | 3/1996 | Howland | 606/61 |
| 5,505,732 A | 4/1996 | Michelson | |
| 5,507,816 A | 4/1996 | Bullivant | |
| 5,514,180 A | 5/1996 | Heggeness et al. | |
| 5,522,899 A | 6/1996 | Michelson | |
| 5,527,312 A | 6/1996 | Ray | |
| 5,531,793 A | 7/1996 | Kelman et al. | |
| 5,534,023 A | 7/1996 | Henley | |
| 5,534,028 A | 7/1996 | Bao et al. | |
| 5,534,029 A | 7/1996 | Shima | |
| 5,534,030 A | 7/1996 | Navarro et al. | |
| 5,534,031 A | 7/1996 | Matsuzaki et al. | |
| 5,540,689 A | 7/1996 | Sanders et al. | |
| 5,545,229 A | 8/1996 | Parsons et al. | |
| 5,549,679 A | 8/1996 | Kuslich | |
| 5,554,191 A | 9/1996 | Lahille et al. | |
| 5,556,431 A | 9/1996 | Buttner-Janz | |
| 5,562,736 A | 10/1996 | Ray et al. | |
| 5,562,738 A | 10/1996 | Boyd et al. | |
| 5,571,109 A | 11/1996 | Bertagnoli | |
| 5,571,189 A | 11/1996 | Kuslich | |
| 5,571,190 A | 11/1996 | Ulrich et al. | |
| 5,571,192 A | 11/1996 | Schönhöffer | |
| 5,591,235 A | 1/1997 | Kuslich | |
| 5,593,409 A | 1/1997 | Michelson | |
| 5,599,279 A | 2/1997 | Slotman et al. | |
| 5,601,556 A | 2/1997 | Pisharodi | |
| 5,609,634 A | 3/1997 | Voydeville | 623/17 |
| 5,609,635 A | 3/1997 | Michelson | |
| 5,609,636 A | 3/1997 | Kohrs et al. | |
| 5,620,458 A | 4/1997 | Green et al. | |
| 5,645,592 A | 7/1997 | Nicolais et al. | |
| 5,645,596 A | 7/1997 | Kim et al. | |
| 5,645,597 A | 7/1997 | Krapiva | |
| 5,645,598 A | 7/1997 | Brosnahan, III | |
| 5,653,761 A | 8/1997 | Pisharodi | |
| 5,653,762 A | 8/1997 | Pisharodi | |

| | | | | | | |
|---|---|---|---|---|---|---|
| 5,658,335 A | 8/1997 | Allen | | 6,022,376 A | 2/2000 | Assell et al. |
| 5,658,336 A | 8/1997 | Pisharodi | | 6,039,761 A | 3/2000 | Li et al. |
| 5,658,337 A | 8/1997 | Kohrs et al. | | 6,039,763 A | 3/2000 | Shelokov |
| 5,669,909 A | 9/1997 | Zdeblick et al. | | 6,042,582 A | 3/2000 | Ray |
| 5,674,294 A | 10/1997 | Bainville et al. | | 6,045,579 A | 4/2000 | Hochshuler et al. |
| 5,674,295 A | 10/1997 | Ray et al. | | 6,045,580 A | 4/2000 | Scarborough et al. |
| 5,674,296 A | 10/1997 | Bryan et al. | | 6,048,342 A | 4/2000 | Zucherman |
| 5,676,701 A | 10/1997 | Yuan et al. | | 6,051,648 A | 4/2000 | Rhee et al. |
| 5,676,702 A | 10/1997 | Ratron | | 6,068,630 A | 5/2000 | Zucherman |
| 5,683,463 A | 11/1997 | Godefroy et al. | | 6,074,390 A | 6/2000 | Zucherman et al. |
| 5,683,464 A | 11/1997 | Wagner et al. | | 6,080,155 A | 6/2000 | Michelson |
| 5,683,465 A | 11/1997 | Shinn et al. | | 6,080,158 A | 6/2000 | Lin |
| 5,693,100 A | 12/1997 | Pisharodi | | 6,080,193 A | 6/2000 | Hochshuler et al. |
| 5,697,889 A | 12/1997 | Slotman et al. | | 6,086,613 A | 7/2000 | Camino et al. |
| 5,697,977 A | 12/1997 | Pisharodi | | 6,090,112 A | 7/2000 | Zucherman et al. |
| 5,700,292 A | 12/1997 | Margulies | | 6,093,205 A | 7/2000 | McLeod et al. |
| 5,702,449 A | 12/1997 | McKay | | 6,096,038 A | 8/2000 | Michelson |
| 5,702,450 A | 12/1997 | Bisserie | | 6,096,080 A | 8/2000 | Nicholson et al. |
| 5,702,454 A | 12/1997 | Baumgartner | | 6,099,531 A | 8/2000 | Bonutti |
| 5,702,455 A | 12/1997 | Saggar | | 6,102,950 A * | 8/2000 | Vaccaro .................. 623/17.16 |
| 5,716,415 A | 2/1998 | Steffee | | 6,110,210 A | 8/2000 | Norton et al. |
| 5,716,416 A | 2/1998 | Lin | | 6,111,164 A | 8/2000 | Rainey et al. |
| 5,741,253 A | 4/1998 | Michelson | | 6,113,637 A | 9/2000 | Gill et al. |
| 5,755,732 A | 5/1998 | Green et al. | | 6,113,638 A | 9/2000 | Williams et al. |
| 5,755,796 A | 5/1998 | Ibo et al. | | 6,113,639 A | 9/2000 | Ray et al. |
| 5,755,798 A | 5/1998 | Papavero et al. | | 6,120,502 A | 9/2000 | Michelson |
| 5,766,252 A | 6/1998 | Henry et al. | | 6,120,503 A | 9/2000 | Michelson |
| 5,772,661 A | 6/1998 | Michelson | | 6,123,705 A | 9/2000 | Michelson |
| 5,776,196 A | 7/1998 | Matsuzaki et al. | | 6,126,689 A | 10/2000 | Brett |
| 5,776,199 A | 7/1998 | Michelson | | 6,127,597 A | 10/2000 | Beyar et al. |
| 5,782,830 A | 7/1998 | Farris | | 6,129,763 A | 10/2000 | Chauvin et al. |
| 5,782,832 A | 7/1998 | Larsen et al. | | 6,132,430 A | 10/2000 | Wagner |
| 5,782,919 A | 7/1998 | Zdeblick et al. | | 6,132,465 A | 10/2000 | Ray et al. |
| 5,797,909 A | 8/1998 | Michelson | | 6,136,001 A | 10/2000 | Michelson |
| 5,800,438 A | 9/1998 | Tuke et al. | | 6,136,031 A | 10/2000 | Middleton |
| 5,800,550 A | 9/1998 | Sertich | | 6,139,579 A | 10/2000 | Steffee et al. |
| 5,824,093 A | 10/1998 | Ray et al. | | 6,146,421 A | 11/2000 | Gordon et al. |
| 5,824,094 A | 10/1998 | Serhan et al. | | 6,146,422 A | 11/2000 | Lawson |
| 5,827,328 A | 10/1998 | Buttermann | | 6,149,650 A | 11/2000 | Michelson |
| 5,836,948 A | 11/1998 | Zucherman et al. | | 6,149,652 A | 11/2000 | Zucherman et al. |
| 5,860,973 A | 1/1999 | Michelson | | 6,149,686 A | 11/2000 | Kuslich et al. |
| 5,860,977 A | 1/1999 | Zucherman et al. | | 6,152,926 A | 11/2000 | Zucherman et al. |
| 5,865,845 A | 2/1999 | Thalgott | | 6,156,038 A | 12/2000 | Zucherman et al. |
| 5,865,846 A | 2/1999 | Bryan et al. | | 6,156,067 A | 12/2000 | Bryan et al. |
| 5,876,404 A | 3/1999 | Zucherman et al. | | 6,159,215 A | 12/2000 | Urbahns et al. |
| 5,885,292 A | 3/1999 | Moskovitz et al. | | 6,162,252 A | 12/2000 | Kuras et al. |
| 5,885,299 A | 3/1999 | Winslow et al. | | 6,165,218 A | 12/2000 | Husson et al. |
| 5,888,222 A | 3/1999 | Coates et al. | | 6,176,882 B1 | 1/2001 | Biedermann et al. |
| 5,888,224 A | 3/1999 | Beckers et al. | | 6,179,874 B1 | 1/2001 | Cauthen |
| 5,888,226 A | 3/1999 | Rogozinski | | 6,183,471 B1 | 2/2001 | Zucherman et al. |
| 5,891,147 A | 4/1999 | Moskovitz et al. | | 6,190,387 B1 | 2/2001 | Zucherman et al. |
| 5,893,889 A | 4/1999 | Harrington | | 6,190,414 B1 | 2/2001 | Young et al. |
| 5,893,890 A | 4/1999 | Pisharodi | | 6,193,757 B1 | 2/2001 | Foley et al. |
| 5,895,426 A | 4/1999 | Scarborough et al. | | 6,206,922 B1 | 3/2001 | Zdeblick et al. |
| 5,895,427 A | 4/1999 | Kuslich et al. | | 6,210,412 B1 | 4/2001 | Michelson |
| 5,895,428 A | 4/1999 | Berry | | 6,224,595 B1 | 5/2001 | Michelson |
| 5,899,941 A | 5/1999 | Nishijima et al. | | 6,224,631 B1 | 5/2001 | Kohrs |
| 5,906,616 A | 5/1999 | Pavlov et al. | | 6,228,118 B1 | 5/2001 | Gordon |
| 5,919,235 A | 7/1999 | Husson et al. | | 6,231,609 B1 | 5/2001 | Mehdizadeh |
| 5,928,284 A | 7/1999 | Mehdizadeh | | 6,234,705 B1 | 5/2001 | Troxell |
| 5,944,754 A | 8/1999 | Vacanti | | 6,235,030 B1 | 5/2001 | Zucherman et al. |
| 5,945,115 A | 8/1999 | Dunn et al. | | 6,238,397 B1 | 5/2001 | Zucherman et al. |
| 5,961,554 A | 10/1999 | Jamson et al. | | 6,241,769 B1 | 6/2001 | Nicholson et al. |
| 5,964,807 A | 10/1999 | Gan et al. | | 6,241,770 B1 | 6/2001 | Michelson |
| 5,976,186 A | 11/1999 | Bao et al. | | 6,241,771 B1 | 6/2001 | Gresser et al. |
| 5,980,572 A | 11/1999 | Kim et al. | | 6,245,072 B1 | 6/2001 | Zdeblick et al. |
| 5,984,967 A | 11/1999 | Zdeblick et al. | | 6,245,108 B1 | 6/2001 | Biscup |
| 5,989,291 A | 11/1999 | Ralph et al. | | 6,261,296 B1 | 7/2001 | Aebi et al. |
| 6,001,130 A | 12/1999 | Bryan et al. | | 6,264,655 B1 | 7/2001 | Pisharodi |
| 6,004,573 A | 12/1999 | Rathi et al. | | 6,264,656 B1 | 7/2001 | Michelson |
| 6,005,162 A | 12/1999 | Constantz | | 6,264,695 B1 | 7/2001 | Stoy |
| 6,019,792 A | 2/2000 | Cauthen | | 6,270,498 B1 | 8/2001 | Michelson |
| 6,019,793 A | 2/2000 | Perren et al. | | 6,277,149 B1 | 8/2001 | Boyle et al. |

| | | |
|---|---|---|
| 6,280,444 B1 | 8/2001 | Zuckerman et al. |
| 6,280,475 B1 | 8/2001 | Bao et al. |
| 6,287,343 B1 | 9/2001 | Kuslich et al. |
| 6,290,724 B1 | 9/2001 | Marino |
| 6,296,664 B1 | 10/2001 | Middleton |
| 6,296,665 B1 | 10/2001 | Strnad et al. |
| 6,302,914 B1 | 10/2001 | Michelson |
| 6,309,421 B1 | 10/2001 | Pisharodi |
| 6,311,562 B1 | 11/2001 | Hanada |
| 6,315,795 B1 | 11/2001 | Scarborough et al. |
| 6,315,797 B1 | 11/2001 | Middleton |
| 6,325,827 B1 | 12/2001 | Lin |
| 6,332,882 B1 | 12/2001 | Zuckerman et al. |
| 6,332,883 B1 | 12/2001 | Zuckerman et al. |
| 6,332,894 B1 | 12/2001 | Stalcup et al. |
| 6,342,074 B1 | 1/2002 | Simpson |
| 6,348,071 B1 | 2/2002 | Steffee et al. |
| 6,350,283 B1 | 2/2002 | Michelson |
| 6,364,880 B1 | 4/2002 | Michelson |
| 6,368,350 B1 | 4/2002 | Erickson et al. |
| 6,368,351 B1 | 4/2002 | Glenn et al. |
| 6,371,984 B1 | 4/2002 | Van Dyke et al. |
| 6,371,988 B1 | 4/2002 | Pafford et al. |
| 6,371,989 B1 | 4/2002 | Chauvin et al. |
| 6,379,355 B1 | 4/2002 | Zuckerman et al. |
| 6,379,385 B1 | 4/2002 | Kalas et al. |
| 6,383,221 B1 | 5/2002 | Scarborough et al. |
| 6,391,030 B1 | 5/2002 | Wagner et al. |
| 6,391,058 B1 | 5/2002 | Kuslich et al. |
| 6,395,030 B1 | 5/2002 | Songer et al. |
| 6,395,031 B1 | 5/2002 | Foley et al. |
| 6,395,032 B1 | 5/2002 | Gauchet |
| 6,395,034 B1 | 5/2002 | Suddaby |
| 6,402,785 B1 | 6/2002 | Zdeblick et al. |
| 6,409,766 B1 | 6/2002 | Brett |
| 6,413,278 B1 | 7/2002 | Marchosky |
| 6,416,551 B1 | 7/2002 | Keller |
| 6,419,676 B1 | 7/2002 | Zuckerman et al. |
| 6,419,677 B1 | 7/2002 | Zuckerman et al. |
| 6,419,704 B1 | 7/2002 | Ferree |
| 6,419,706 B1 | 7/2002 | Graf |
| 6,423,063 B1 | 7/2002 | Bonutti |
| 6,423,095 B1 | 7/2002 | Van Hoech et al. |
| 6,425,920 B1 | 7/2002 | Hamada |
| 6,432,106 B1 | 8/2002 | Fraser |
| 6,436,098 B1 | 8/2002 | Michelson |
| 6,436,119 B1 | 8/2002 | Erb et al. |
| 6,436,140 B1 | 8/2002 | Liu et al. |
| 6,436,142 B1 | 8/2002 | Paes et al. |
| 6,440,168 B1 | 8/2002 | Cauthen |
| 6,443,990 B1 | 9/2002 | Aebi et al. |
| 6,447,512 B1 | 9/2002 | Landry et al. |
| 6,447,544 B1 | 9/2002 | Michelson |
| 6,447,547 B1 | 9/2002 | Michelson |
| 6,451,019 B1 | 9/2002 | Zuckerman et al. |
| 6,451,020 B1 | 9/2002 | Zuckerman et al. |
| 6,454,804 B1 | 9/2002 | Ferree |
| 6,454,807 B1 | 9/2002 | Jackson |
| 6,458,131 B1 | 10/2002 | Ray |
| 6,458,159 B1 | 10/2002 | Thalgott |
| 6,461,359 B1 | 10/2002 | Tribus et al. |
| 6,468,310 B1 | 10/2002 | Ralph et al. |
| 6,471,724 B1 | 10/2002 | Zdeblick et al. |
| 6,475,219 B1 | 11/2002 | Shelokov |
| 6,478,796 B1 | 11/2002 | Zuckerman et al. |
| 6,478,822 B1 | 11/2002 | Leroux et al. |
| 6,478,823 B1 | 11/2002 | Michelson |
| 6,482,233 B1 | 11/2002 | Aebi et al. |
| 6,482,235 B1 | 11/2002 | Lambrecht et al. |
| 6,485,517 B1 | 11/2002 | Michelson |
| 6,488,710 B1 | 12/2002 | Besselink |
| 6,500,178 B1 | 12/2002 | Zuckerman et al. |
| 6,500,205 B1 | 12/2002 | Michelson |
| 6,503,279 B1 | 1/2003 | Webb et al. |
| 6,514,256 B1 | 2/2003 | Zuckerman et al. |
| 6,517,580 B1 | 2/2003 | Ramadan et al. |
| 6,520,993 B1 | 2/2003 | James et al. |
| 6,520,996 B1 | 2/2003 | Manasas et al. |
| 6,524,312 B1 | 2/2003 | Landry et al. |
| 6,527,773 B1 | 3/2003 | Lin et al. |
| 6,527,804 B1 | 3/2003 | Gauchet et al. |
| 6,527,806 B1 | 3/2003 | Ralph et al. |
| 6,530,933 B1 | 3/2003 | Yeung et al. |
| 6,530,955 B1 | 3/2003 | Boyle et al. |
| 6,540,785 B1 | 4/2003 | Gill et al. |
| 6,547,823 B1 | 4/2003 | Scarborough et al. |
| 6,548,002 B1 | 4/2003 | Gresser et al. |
| 6,554,863 B1 | 4/2003 | Paul et al. |
| 6,558,386 B1 | 5/2003 | Cragg |
| 6,558,387 B1 | 5/2003 | Errico et al. |
| 6,558,390 B1 | 5/2003 | Cragg |
| 6,558,423 B1 | 5/2003 | Michelson |
| 6,558,424 B1 | 5/2003 | Thalgott |
| 6,562,073 B1 | 5/2003 | Foley |
| 6,562,074 B1 | 5/2003 | Gerbec et al. |
| 6,565,570 B1 | 5/2003 | Sterett et al. |
| 6,569,201 B1 | 5/2003 | Moumene et al. |
| 6,572,653 B1 | 6/2003 | Simonson |
| 6,572,654 B1 | 6/2003 | Santilli |
| 6,575,982 B1 | 6/2003 | Bonutti |
| 6,576,016 B1 | 6/2003 | Hochshuler et al. |
| 6,576,017 B1 | 6/2003 | Foley et al. |
| 6,579,318 B1 | 6/2003 | Varga et al. |
| 6,579,320 B1 | 6/2003 | Gauchet et al. |
| 6,579,321 B1 | 6/2003 | Gordon et al. |
| 6,582,432 B1 | 6/2003 | Michelson |
| 6,582,437 B1 | 6/2003 | Dorchak et al. |
| 6,582,468 B1 | 6/2003 | Gauchet |
| 6,610,089 B1 | 8/2003 | Liu et al. |
| 6,682,562 B1 * | 1/2004 | Viart et al. ............. 623/17.14 |
| 6,706,070 B1 | 3/2004 | Wagner et al. |
| 6,740,118 B1 * | 5/2004 | Eisermann et al. ...... 623/17.14 |
| 6,746,484 B1 | 6/2004 | Liu et al. |
| 6,755,841 B1 | 6/2004 | Fraser et al. |
| 6,770,095 B1 * | 8/2004 | Grinberg et al. ......... 623/17.14 |
| 6,893,466 B1 | 5/2005 | Trieu |
| 2001/0012938 A1 | 8/2001 | Zuckerman et al. |
| 2002/0128715 A1 | 9/2002 | Bryan et al. |
| 2003/0208273 A1 | 11/2003 | Eisermann et al. |
| 2004/0073313 A1 | 4/2004 | Link et al. |
| 2004/0117022 A1 | 6/2004 | Mamay et al. |
| 2004/0138750 A1 * | 7/2004 | Mitchell .................. 623/17.11 |
| 2004/0143332 A1 | 7/2004 | Krueger et al. |

FOREIGN PATENT DOCUMENTS

| | | |
|---|---|---|
| DE | 3113142 | 1/1982 |
| DE | 4012622 | 7/1991 |
| EP | 0307241 B1 | 3/1989 |
| EP | 0322334 | 6/1989 |
| FR | 2722980 | 7/1994 |
| FR | 2705227 | 11/1994 |
| FR | 2707864 | 1/1995 |
| FR | 2717066 | 9/1995 |
| FR | 2717068 | 9/1995 |
| FR | 2722088 | 1/1996 |
| FR | 2724554 | 3/1996 |
| FR | 2730156 A1 | 8/1996 |
| FR | 2780269 A1 | 12/1999 |
| FR | 2805985 * | 9/2001 |
| FR | 2806614 A1 | 9/2001 |
| GB | 780652 | 8/1957 |
| WO | WO 90/00037 | 1/1990 |
| WO | WO 95/31158 A | 11/1995 |
| WO | WO 99/26562 | 6/1999 |

| WO | WO 99/59669 | 11/1999 |
| WO | WO 00/04851 | 2/2000 |
| WO | WO 00/13619 | 3/2000 |
| WO | WO 00/13620 | 3/2000 |
| WO | WO 00/23015 A1 | 4/2000 |
| WO | 01/01893 A1 | 1/2001 |

* cited by examiner

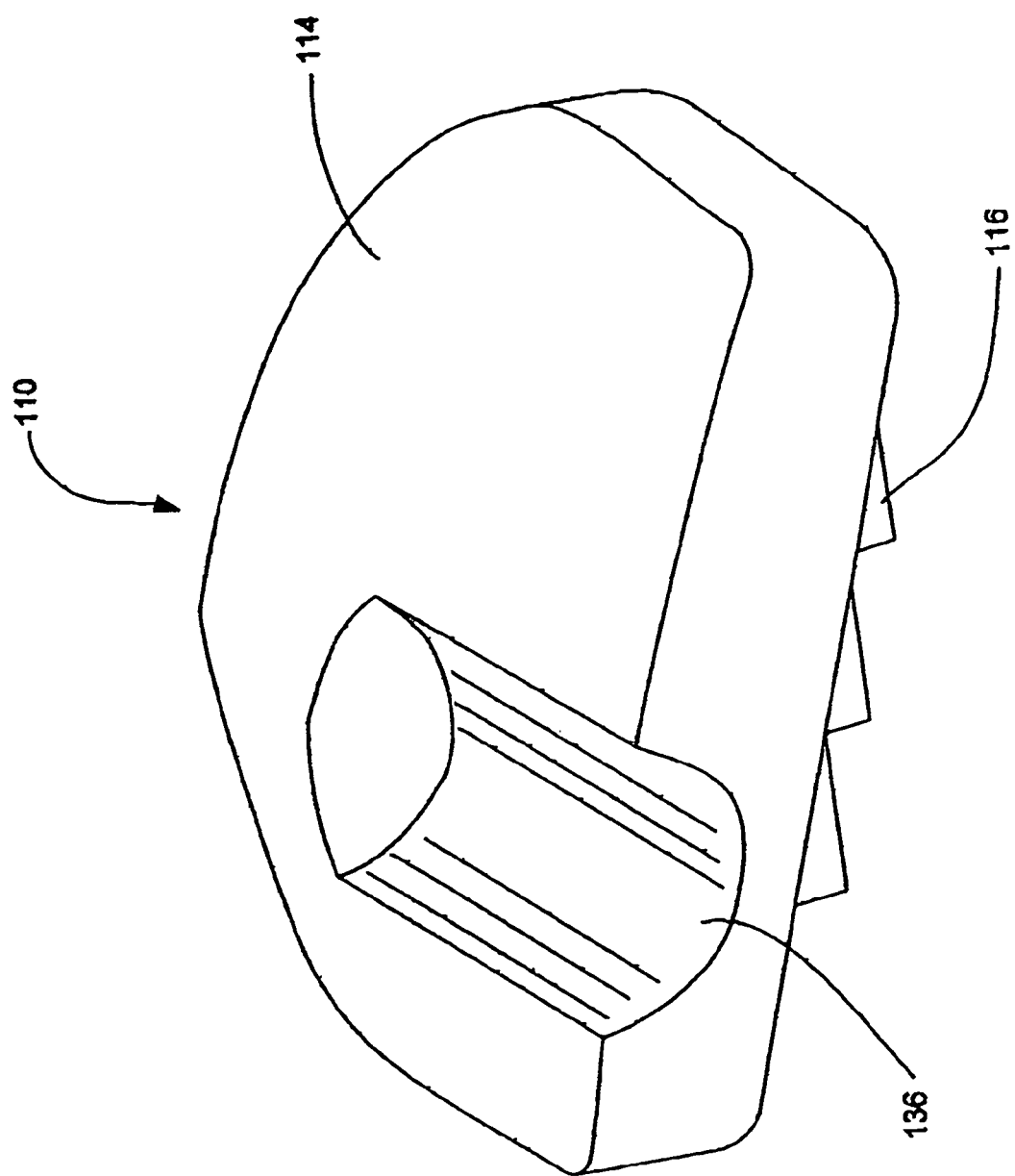

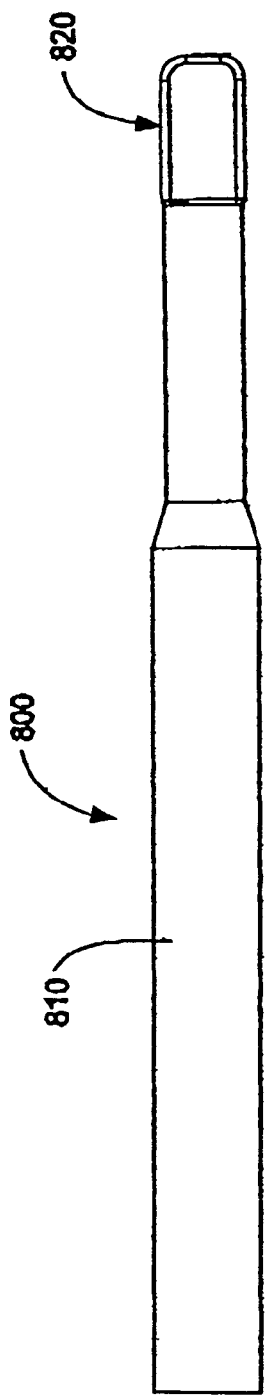
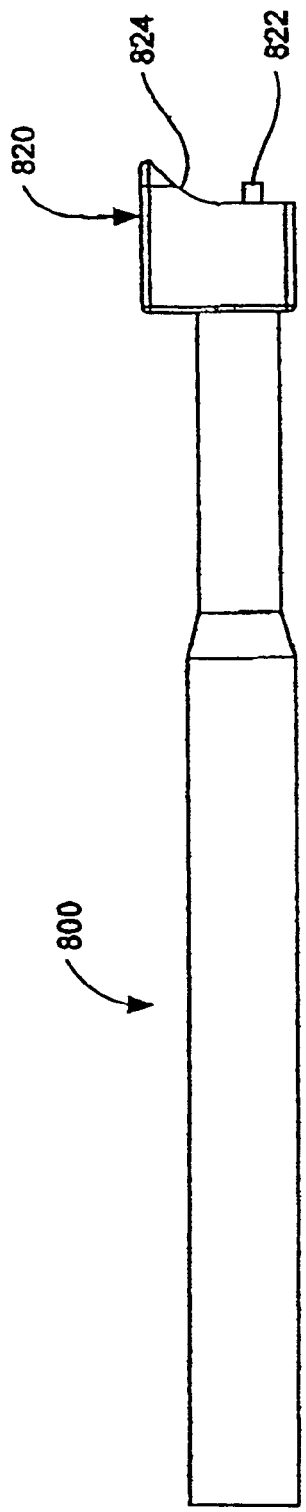
FIG. - 8A
FIG. - 8B

US 7,083,649 B2

ARTIFICIAL VERTEBRAL DISK REPLACEMENT IMPLANT WITH TRANSLATING PIVOT POINT

CLAIM OF PRIORITY

This application claims priority to U.S. Provisional Application No. 60/422,039, filed on Oct. 29, 2002, entitled "ARTIFICIAL VERTEBRAL DISK REPLACEMENT IMPLANT WITH TRANSLATING PIVOT POINT AND METHOD," and which is incorporated herein by reference.

CROSS REFERENCE TO RELATED APPLICATIONS

This application is related to U.S. Provisional Application No. 60/422,021, filed on Oct. 29, 2002, entitled "TOOLS FOR IMPLANTING AN ARTIFICIAL VERTEBRAL DISK AND METHOD", U.S. patent application Ser. No. 10/684,668 filed Oct. 14, 2003, entitled "TOOLS FOR IMPLANTING AN ARTIFICIAL VERTEBRAL DISK AND METHOD", U.S. Provisional Application No. 60/422,011, filed Oct. 29, 2002, entitled "ARTIFICIAL VERTEBRAL DISK REPLACEMENT IMPLANT WITH CROSS BAR SPACER AND METHOD", U.S. patent application Ser. No. 10/685,134 filed Oct. 14, 2003, entitled "ARTIFICIAL VERTEBRAL DISK REPLACEMENT IMPLANT WITH CROSS BAR SPACER AND METHOD", U.S. Provisional Application No. 60/422,022, filed Oct. 29, 2002, entitled "ARTIFICIAL VERTEBRAL DISK REPLACEMENT IMPLANT WITH SPACER AND METHOD," and U.S. patent application Ser. No. 10/685,011 filed Oct. 14, 2003, entitled "ARTIFICIAL VERTEBRAL DISK REPLACEMENT IMPLANT WITH SPACER AND METHOD," which are incorporated herein by reference.

FIELD OF THE INVENTION

This invention relates to an artificial vertebral disk replacement, a method of operation, and a method of implanting.

BACKGROUND OF THE INVENTION

As the present society ages, it is anticipated that there will be an increase in degenerative and dysfunctional spinal disk conditions. Pain associated with such disk conditions can be relieved by medication and/or surgery.

Over the years, a variety of intervertebral implants have been developed in an effort to relieve the pain associated with such degenerative and dysfunctional disk conditions. For example, U.S. Pat. No. 4,349,921 to Kuntz discloses an intervertebral disk prosthesis. The Kuntz prosthesis is designed to restore the space between the disks.

U.S. Pat. No. 4,714,469 to Kenna discloses a spinal implant that fuses vertebrae to the implant. The implant has a rigid body that fits between the vertebrae with a protuberance extending from a vertebral contacting surface and into the vertebral body.

U.S. Pat. No. 5,258,031 to Salib et al. discloses another prosthetic disk with a ball that fits into a socket.

U.S. Pat. Nos. 5,425,773 and 5,562,738 are related patents to Boyd et al. that disclose a disk arthroplasty device for replacement of the spinal disk. A ball-and-socket are provided to enable rotation.

U.S. Pat. No. 5,534,029 to Shima discloses an articulated vertebral body spacer with a pair of upper and lower joint pieces inserted between the vertebrae. An intermediate layer is provided to allow for movement between the upper joint piece and the lower joint piece.

U.S. Pat. No. 5,782,832 to Larsen et al. discloses a two-piece ball-and-socket spinal implant with upper and lower plates for insertion within the intervertebral space.

U.S. Pat. No. 6,156,067 to Bryan et al. discloses a prosthesis having two plates with a nucleus therebetween.

None of these solutions provide an implant that restores a wide range of natural movement.

Accordingly, what is needed is an implant for alleviating such conditions and that restores natural movement.

SUMMARY OF THE INVENTION

The present invention includes embodiments that are directed to an implant for alleviating discomfort associated with the spinal column. One embodiment of the implant includes a first plate with an elongated socket and a second plate that mates with the first plate and has an elongated ball. The implant is designed to replace the disk between two vertebrae.

Other aspects, objects, features, and elements of the other embodiments of the invention are described or are evident from the accompanying specification, claims and figures.

BRIEF DESCRIPTION OF THE DRAWINGS

FIG. 4B is a perspective view of a socket portion of the embodiment of the implant of the invention.

FIG. 8A is a side view of an embodiment of the implant insertion tool of the invention. FIG. 8B is a top view of the embodiment of the implant insertion tool of the invention.

DETAILED DESCRIPTION OF THE PREFERRED EMBODIMENTS OF THE INVENTION

The following description is presented to enable any person skilled in the art to make and use the invention. Various modifications to the embodiments described will be readily apparent to those skilled in the art, and the principles defined herein can be applied to other embodiments and applications without departing from the spirit and scope of the present invention as defined by the appended claims. Thus, the present invention is not intended to be limited to the embodiments shown, but is to be accorded the widest scope consistent with the principles and features disclosed herein. To the extent necessary to achieve a complete understanding of the invention disclosed, the specification and drawings of all patents, patent publications, and patent applications cited in this application are incorporated herein by reference.

Figure 1A:
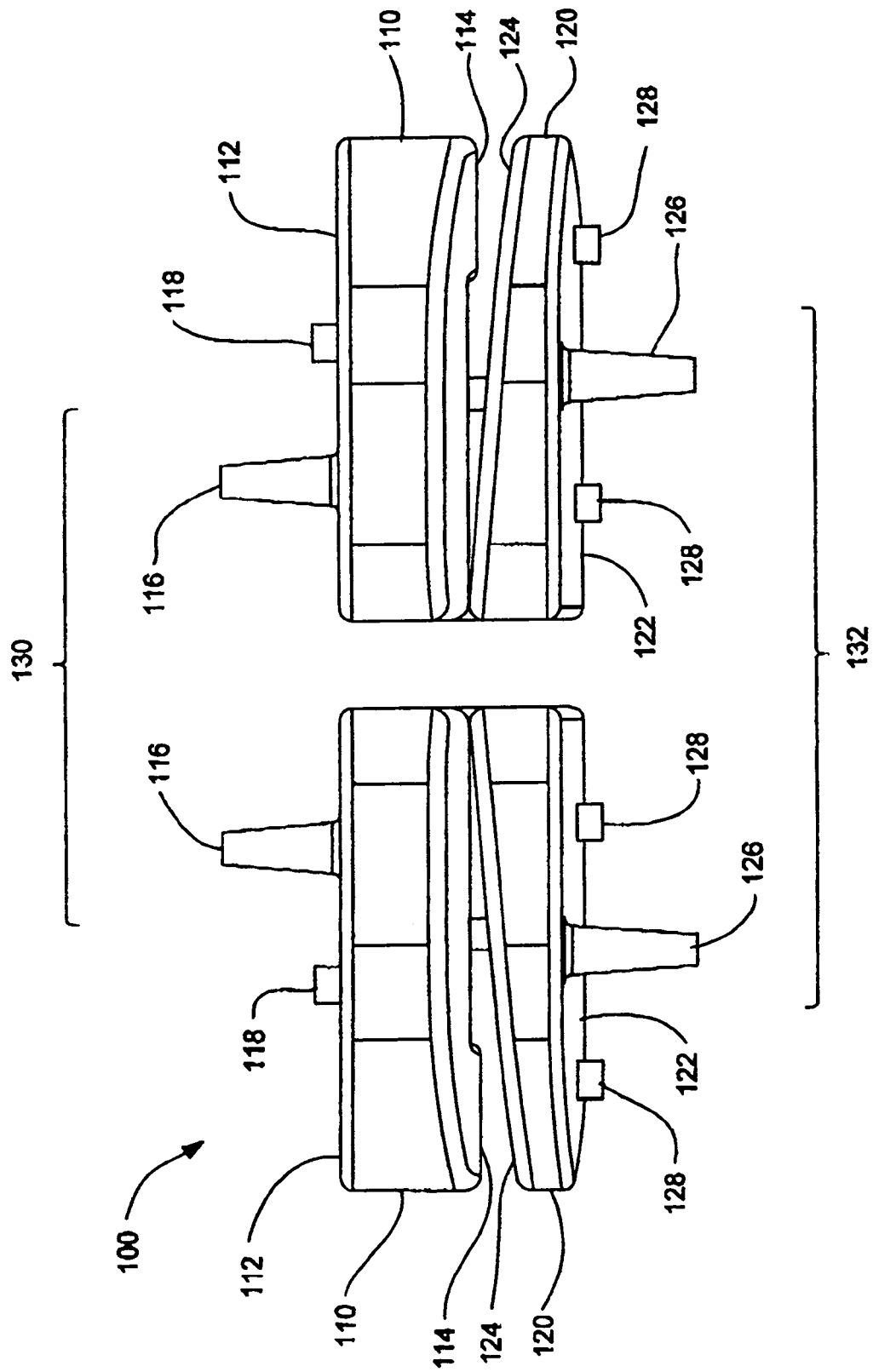
FIG. 1A is a posterior view of an embodiment of the assembled implant of the invention.

Turning now to FIG. 1A, a posterior view of an intervertebral implant 100 is depicted having a four-piece configuration. Although, as will be appreciated by those of skill in the art, other configurations, such as a two-piece configuration or a three-piece configuration, are possible without departing from the scope of the invention. As depicted, the intervertebral implant 100 has a pair 130 of first plates 110. Each first plate 110 has a first surface 112 and a second surface 114. The first surface 112 is configured to abut an end plate surface of a vertebral body. A keel 116 can be provided on the first surface 112 to anchor the first surface 112 into the vertebral body upon implantation. One or more additional protrusions 118 can also be provided that act as a detent or catch, thus providing a further mechanism to prevent the first plate 110 from moving relative to the vertebral body once implanted.

The intervertebral implant 100 also has a pair 132 of second plates 120. The second plates 120 have a first surface 122 and a second surface 124. The first surface 122 is configured to abut an end plate surface of a vertebral body. As with the first plate 110, a keel 126 can be provided on the first surface 122 to anchor the first surface 122 into the vertebral body upon implantation. One or more additional protrusions 128 can also be provided that act as a detent or catch, again providing a further mechanism to prevent the second plate 120 from moving relative to the vertebral body once implanted.

Figure 1B:
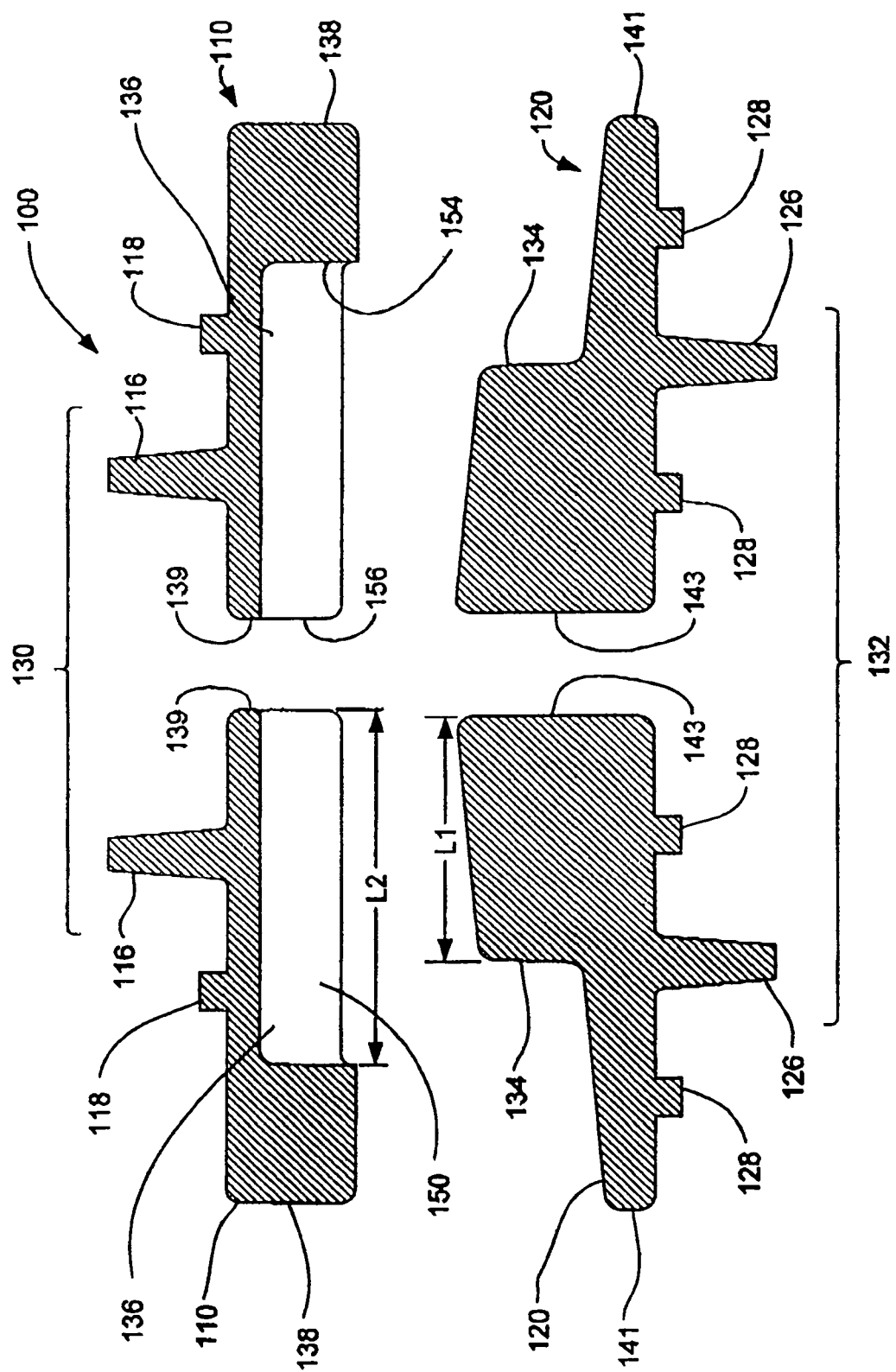
FIG. 1B is a cross-section of the device shown in FIG. 1A.
Figure 3A:
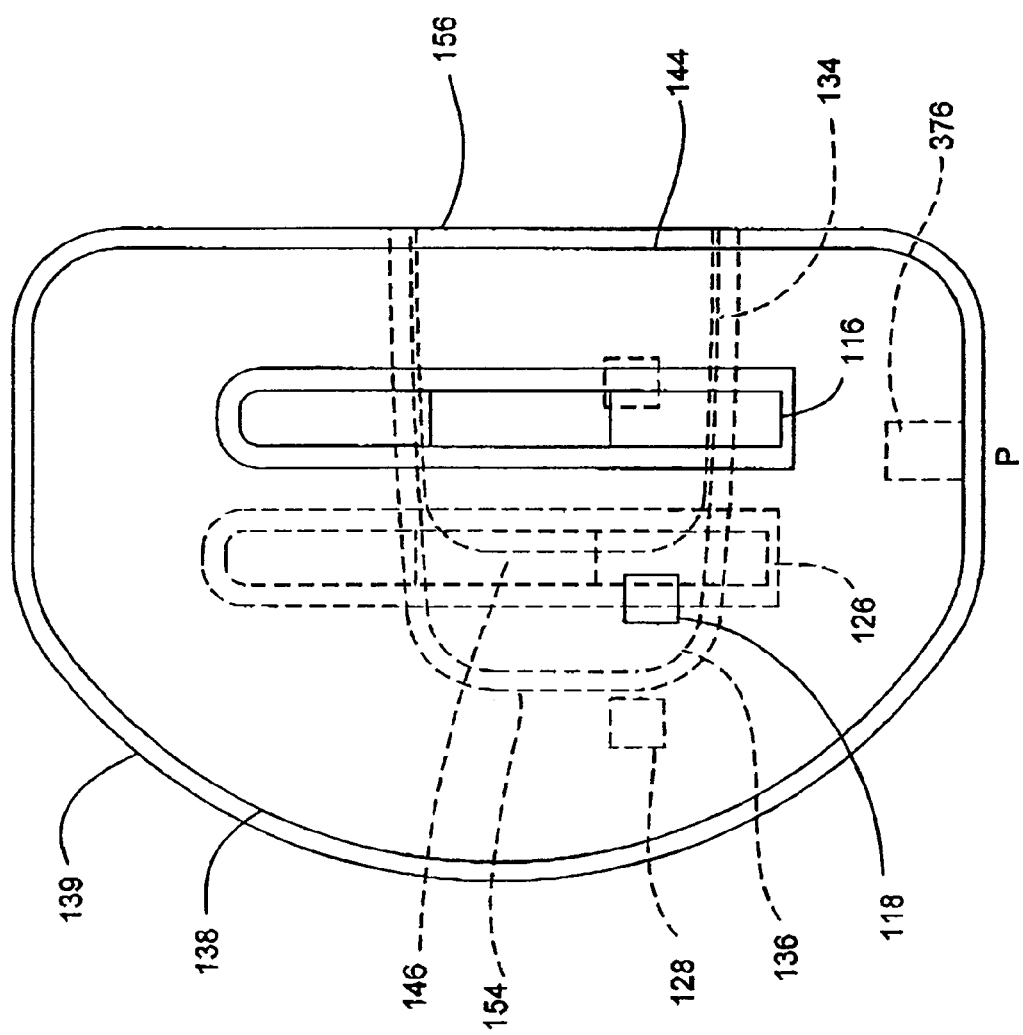
FIG. 3A is a top view of a portion of an embodiment of the assembled implant of the invention.

FIG. 1B depicts the pair 130 of upper plates 110 and the pair 132 of lower plates 120 in cross-section. Each upper plate 110 has a socket 136 that has a first elongated sidewall 150, a corresponding second elongated sidewall 152 (shown in FIG. 3B), an end wall 154, and an open end 156. The open ends 156 of each of the first plates 110 are oriented so that the open ends 156 face each other. The lower plates 120 each have a ball 134. As illustrated in FIG. 1B, the ball 134 is an elongated ball. Each of the plates 110, 120 has a first end 138, 141 and a second end 139, 143, respectively. The ends 139 of the first plate 110 face each other and the ends 143 of the second plate 120 also face each other. The ends 138, 141 are curved and convex, as shown in FIG. 3A, so that the implant 100 has a configuration that correlates to the curved shape of a vertebra.

Figure 1C:
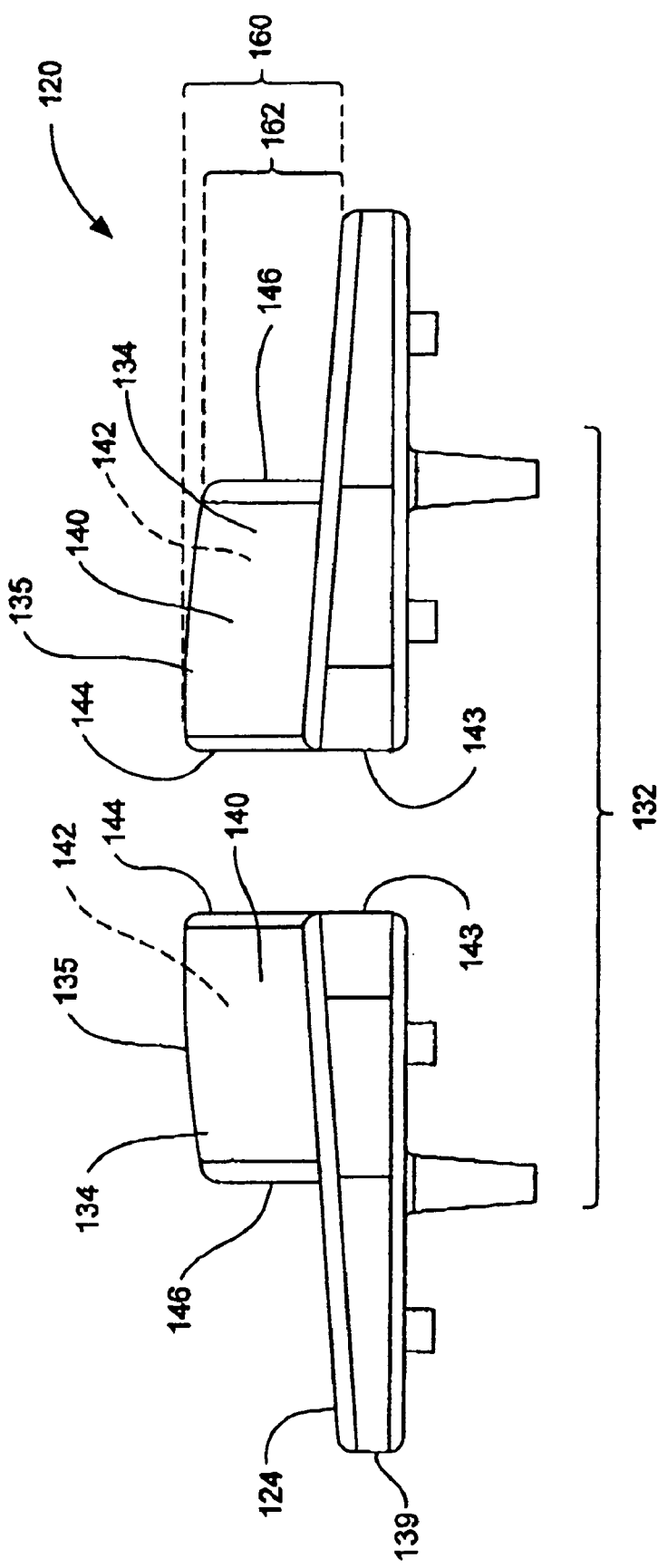
FIG. 1C is a posterior view of two bottom plates of the implant of the embodiment of the invention.

As shown in FIG. 1C, the ball 134 has four sides: a first elongated sidewall 140, a second elongated sidewall 142, a third end wall 143, and a fourth end wall 146. The third end wall 144 is flush with the end 143 of the plate 120 of the implant. The third end wall 144 has a profile height 160 and the fourth end wall 146 has a profile height 162. Comparing the profile heights 160, 162 to each other at the same point on the second surface 124 of the second plate 120, the overall profile height of the third end wall 144 is greater than the fourth end wall 146 (i.e., 160>162). Thus, it is evident that the upper surface 135 of socket 136 slopes downwardly from the end wall 144 to the end wall 146. Together balls 134 comprise a ball structure that has a high surface where the third end walls 144 abut each other and slope to a lower surface adjacent to fourth end walls 146. Also, preferably, the upper surfaces 135 are barrel shaped and have a "U" shaped profile along a cross-section that is perpendicular to the page of FIG. 1C (parallel the sagittal plane on implantation). The sloping upper surface 135, as will be explained later, allows the pair 130 of upper plates 110 to easily slide, or rock, side-to-side on the ball structure and slide, or ride, forward and backward with enough looseness of fit to allow for some twisting in order to emulate the motion of the vertebral bone and intervertebral disk tissue. This arrangement, thus, has a sliding or translating pivot point. Further, as indicated in FIG. 1C the edges are eased or rounded to allow for further range of motion of the pair 130 of plates 110 relative to the pair 132 of plates 120. As will be appreciated by those of skill in the art, the overall height of the third end wall 144 and the fourth end wall 146 can be equivalent while still having an effective third end wall height 160 that is greater than the effective fourth end wall height 162 due to the overall slope of the second surface 124. Alternatively, the overall height of the third end wall 144 and the fourth end wall 146, can be different with the third end wall 144 having a height greater than the fourth end wall 146, thus eliminating the need for the second surface 124 to have a slope or further increasing the net difference between the height of the third end wall and the fourth end wall.

Further, although the ball 134 is depicted such that the third end wall 144 is flush with the second end 143, those of skill in the art will appreciate that the ball 134 could also be configured such that the third end wall 144 was recessed relative to the end 143 of the second plate. In such a configuration, the third end wall 144 and the end 143 would not be flush.

Figure 1D:
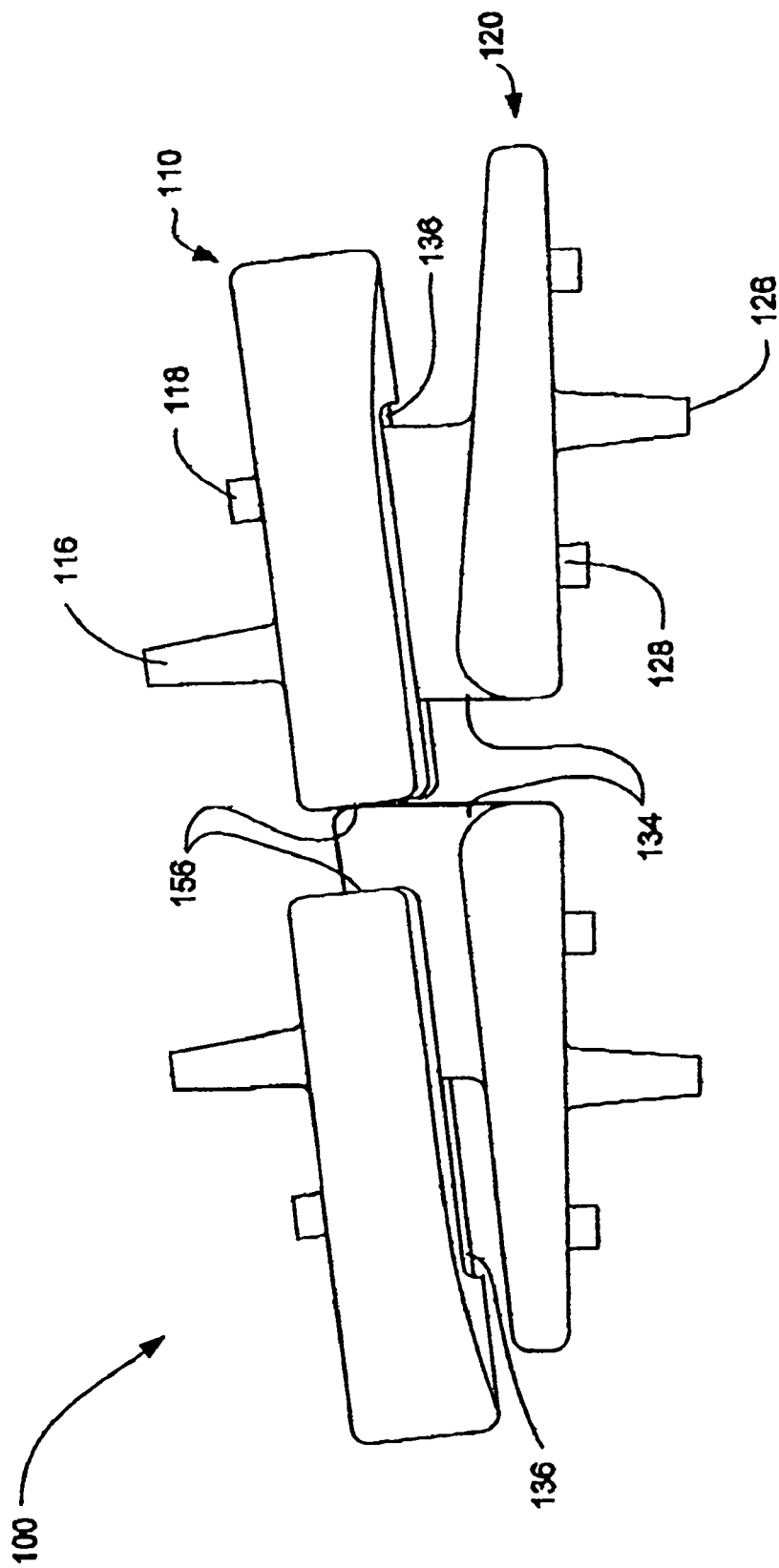
FIGS. 1D and 1E are posterior views of the embodiment of the implant of the invention shown in FIG. 1A illustrating the operation of the device in bending to the left and bending to the right, respectively.
Figure 1E:
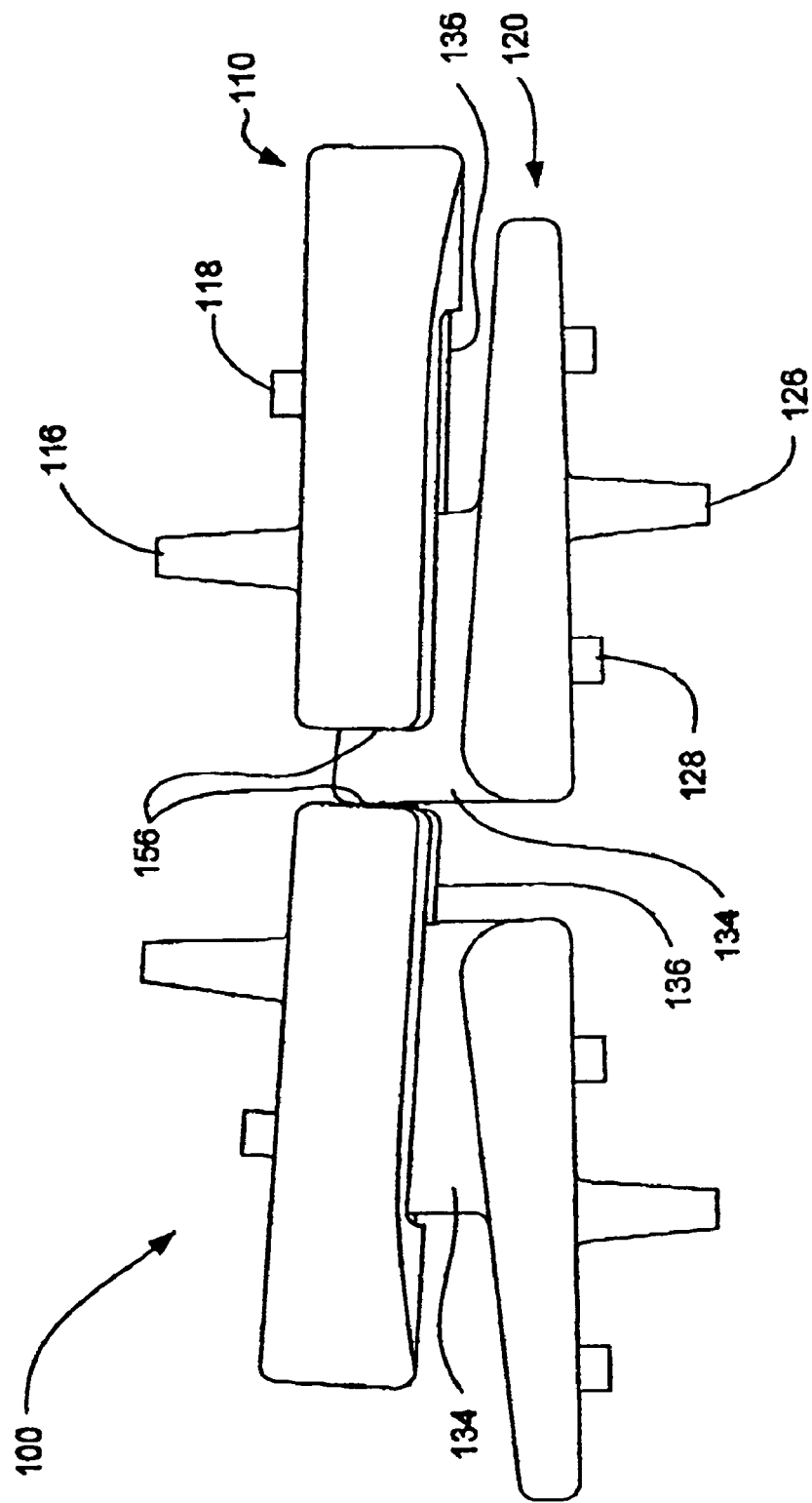

FIGS. 1D and 1E illustrate posterior views of the implant 100 showing the clearance for left and right lateral bending. Typically, left and right lateral bending ranges from 3–5°. As evident from these figures (and FIG. 1B), the length L1 of the ball 134 can be less than the length L2 of the socket 136. Further, as shown, the open ends 156 of the sockets facilitate movement of the balls 134 within the socket 136 to accommodate side-bending movement.

Figure 2A:
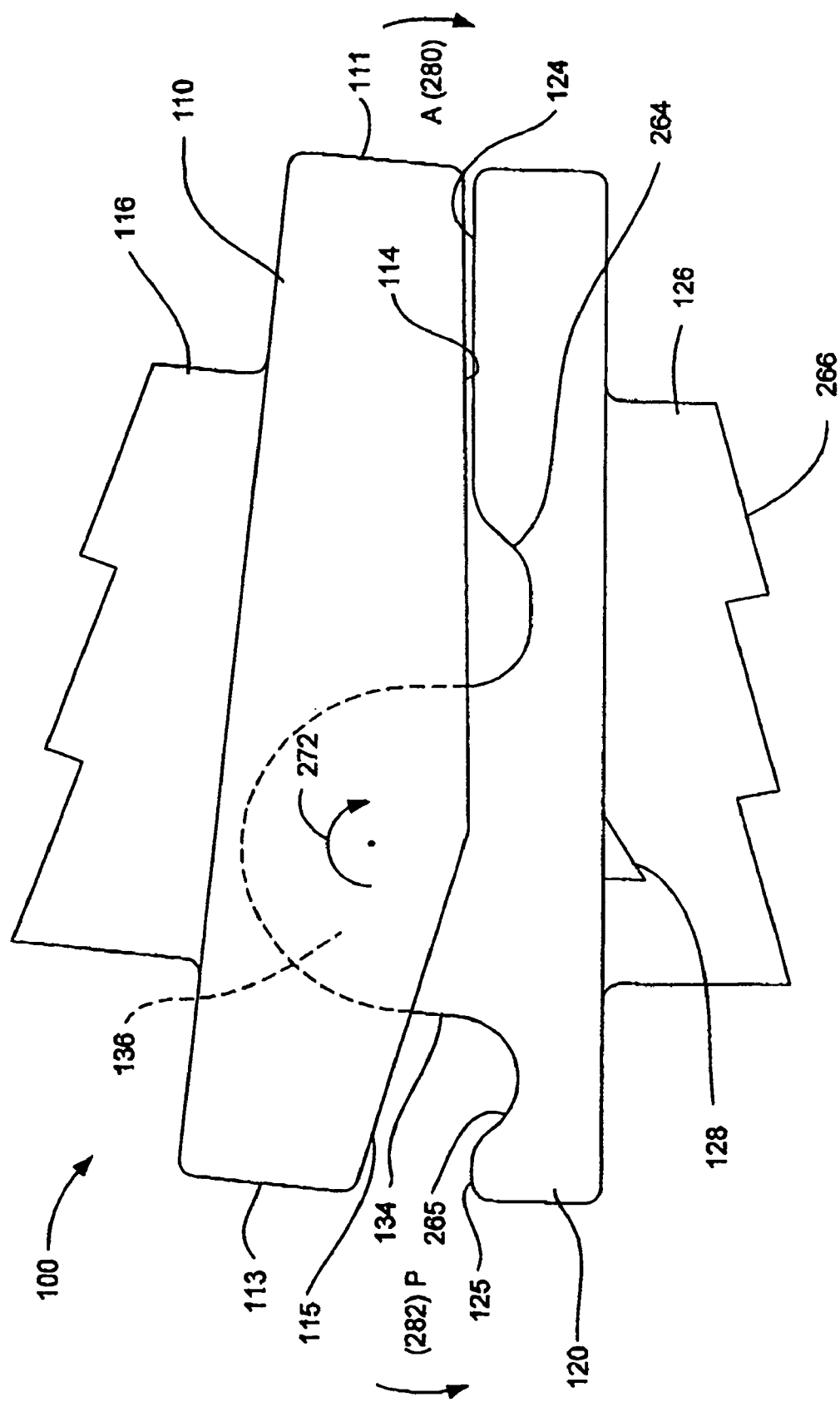
FIG. 2A is a side view of the implant of FIG. 1A showing the implant in flexion.

FIG. 2A is a side view of the intervertebral implant 100. The first plate 110 with this socket 136 and the second plate 120 with the ball portion 134 are depicted. As is apparent from the figure, the sloping of the second surface 114 of the first plate 110 facilitates rotation of the ball-and-socket joint in an anterior "A" 280 direction and a posterior "P" 282 direction. As depicted, the second surface 114 slopes from a high point at about where the socket is located to low points at the ends 111 and 113 of the plate 110. As shown in FIG. 2A, the implant 100 is positioned to achieve flexion 272 (i.e., forward bending) in a range up to about 15°, but more preferably 10°.

As shown in FIG. 2A the second plate 120 can also have channels 264, 265 or a groove adjacent the ball 134. The channels 264, 265 can be configured such that it surrounds a portion of the ball 134 or the entire ball 134. As will be explained below, the channel allows the sides of the ball 134 to be made more perpendicular so as to create a greater blocking wall thus preventing the socket of the upper plate 100 from moving too much anteriorly or posteriorly relative to the lower plate 120.

Either one or both of the keels on the first surface 116 and the second surface 126 can have one or more posteriorly pointing teeth 266 to enable it to more securely engage the vertebral body into which it is implanted. As can be seen in FIG. 2A, the protrusions 128, as well as the additional protrusions 118 (FIG. 1A) can also have posteriorly pointing teeth in order to lock the implant 100 in position in the vertebrae.

Figure 2B:
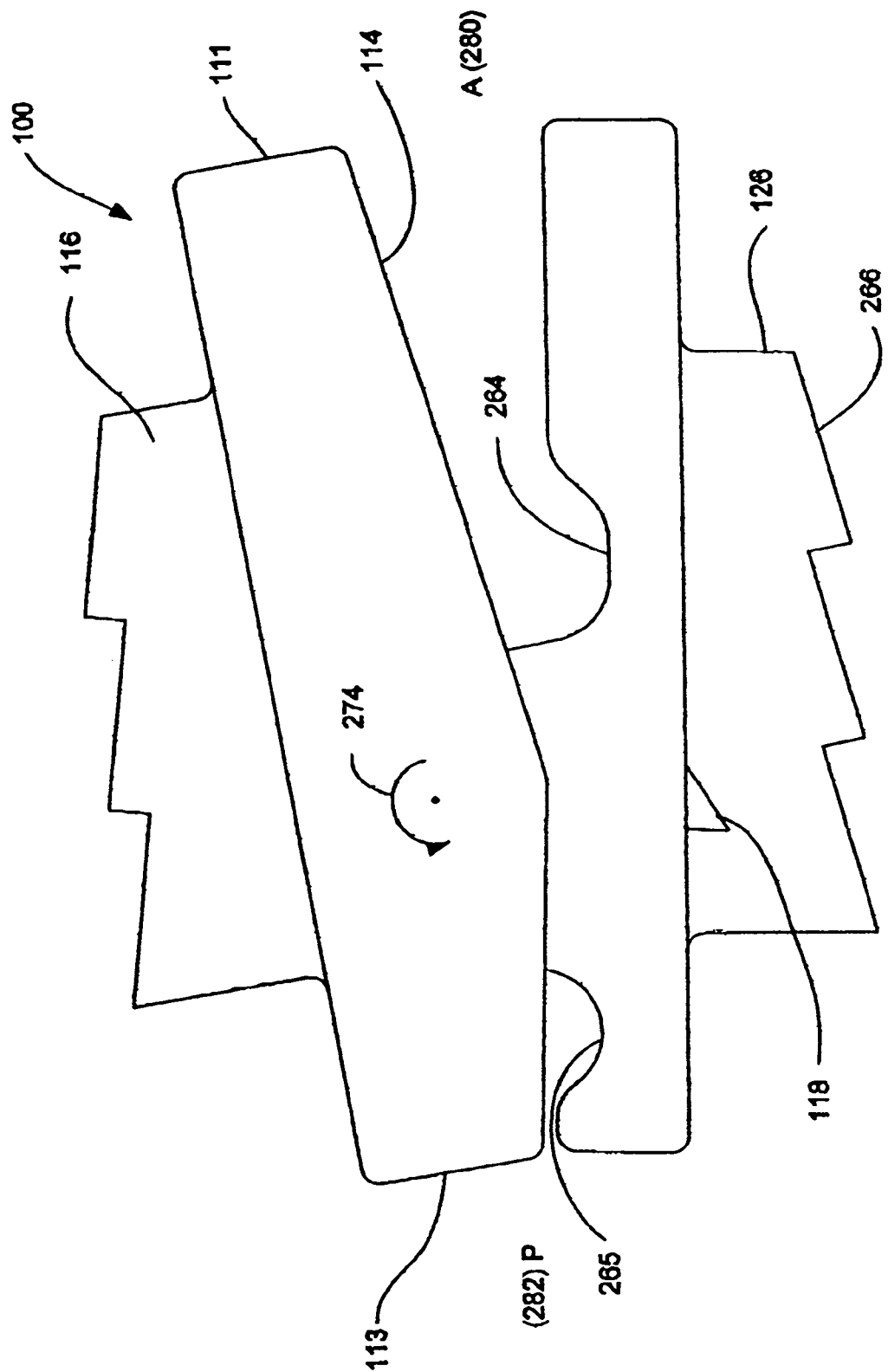
FIG. 2B is a side view of the implant showing the implant in extension.

FIG. 2B is an alternate side view of the intervertebral implant 100 wherein the plates 110, 120 are shown and the ball-and-socket joint is positioned to achieve extension 274 (i.e., backward bending) in a preferable range of up to about 5°.

Figure 2C:
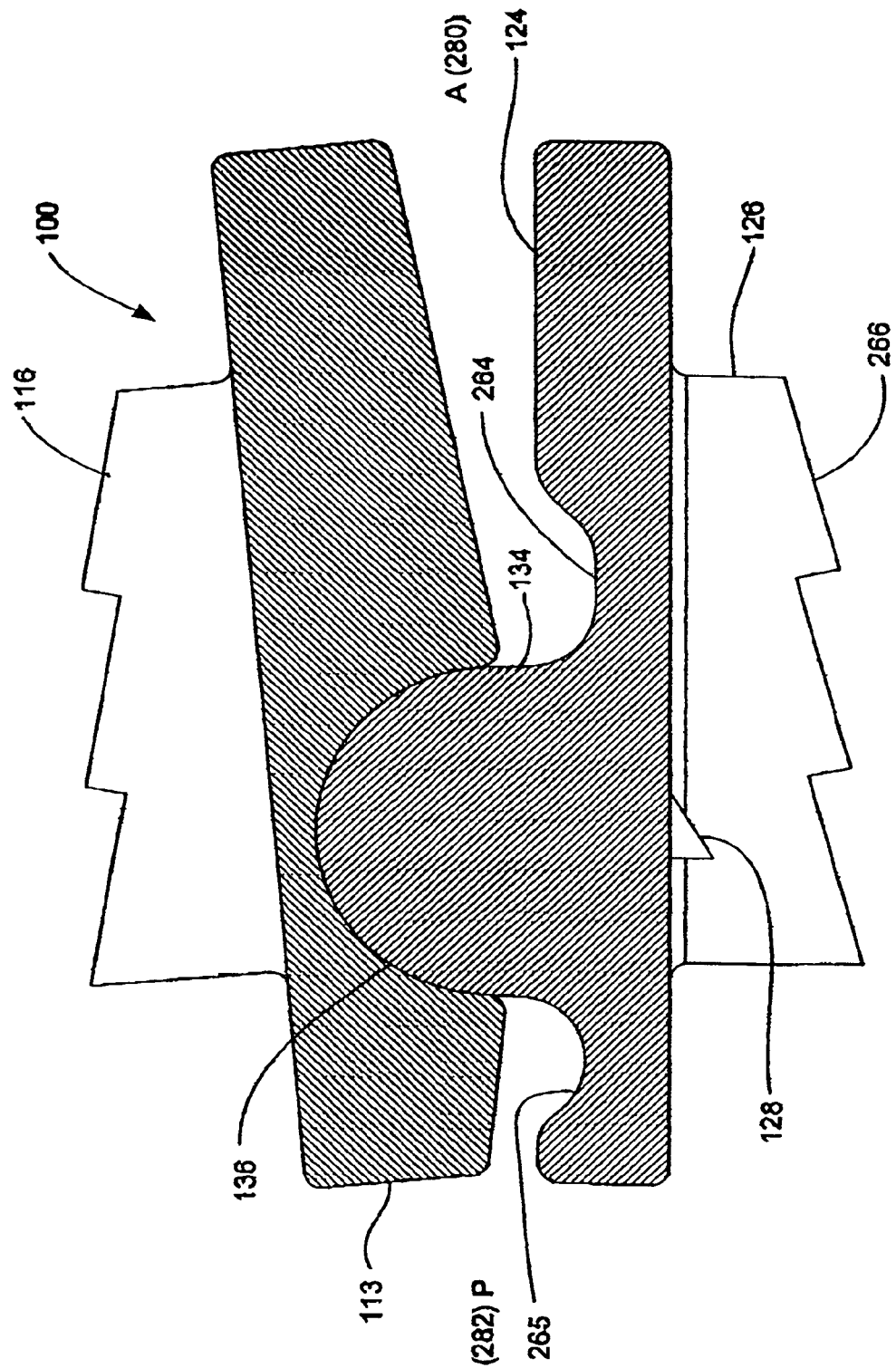
FIG. 2C is a partial cross-sectional view of a side view of the implant of an embodiment of the invention.
Figure 2D:
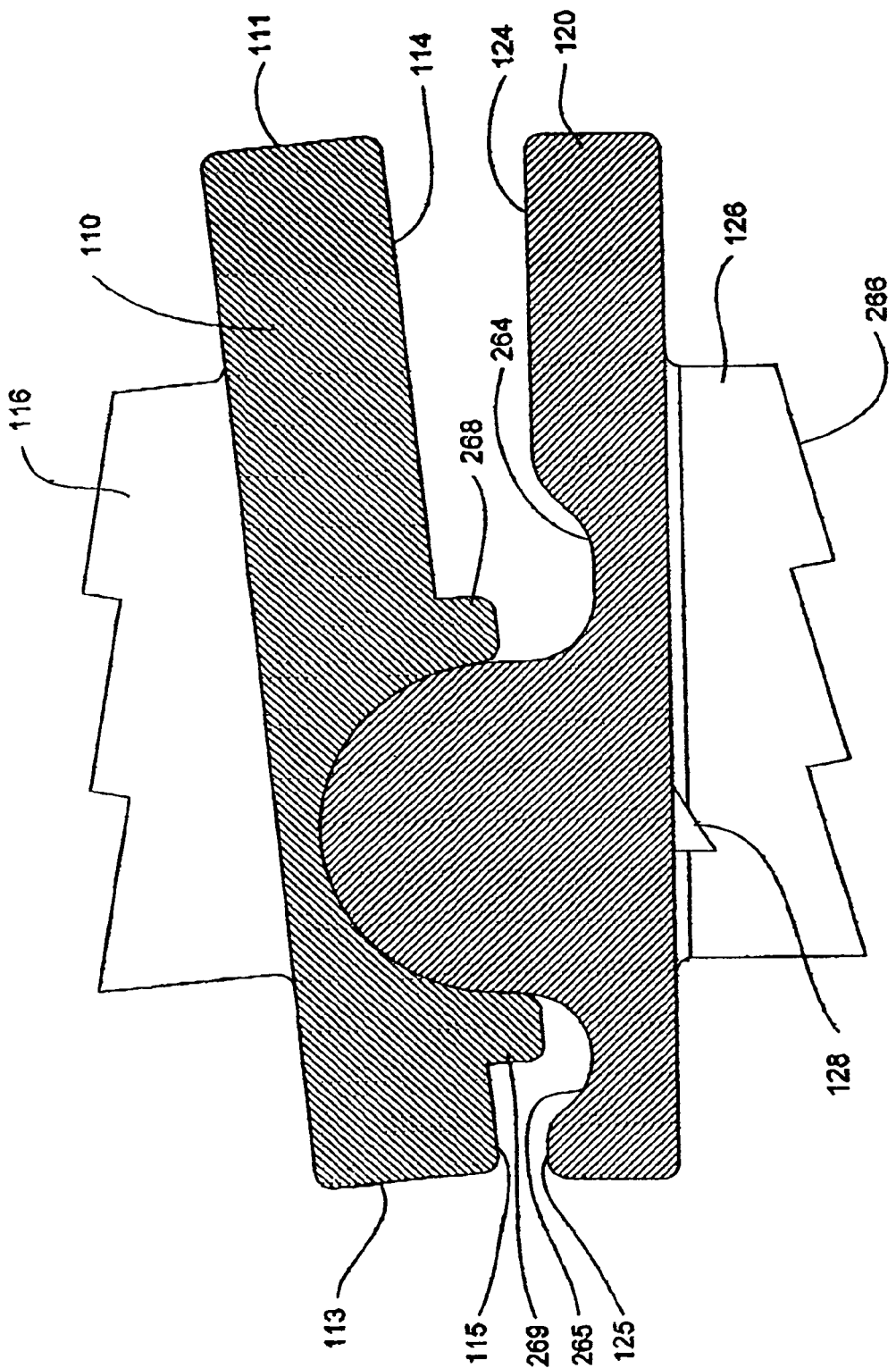
FIG. 2D is a partial cross-sectional view of an alternative embodiment of the implant of the invention having a protuberance adjacent the socket.

FIG. 2C is a cross-section of the side view of the intervertebral implant 100 showing the mating of the ball 134 to the socket 136. FIG. 2D illustrates an alternate embodiment of the first plate 110 wherein the socket 136 has ridges 268, 269 forming a protuberance that extends into the channel 264, 265 respectively on the second plate 120. As will be appreciated by those of skill in the art, the protuberances 268, 269 can extend partially into the channel, such as the configuration shown, or can have a channel conforming shape such that when the ball-and-socket joint are moved to achieve flexion 272 or extension 274 the protuberance or ridge 268, 269 extends into the channels 264, 265. This embodiment allows the surfaces 114 and 115 of the first plate 110 and the second plate 115 to be flat and non-sloping as shown while still allowing for the implant to emulate forward and backward bending and allow for the blocking of the motion of the socket relative to the ball.

Turning now to FIG. 3A, a top view of one-half of the intervertebral implant 100 is shown. Each of the top first plate 110 and the bottom second plate 120 have a bore 376 for receiving a pin of an implant tool. The keel 116 on the first plate 110 is positioned so that it is does not align in the same plane with the keel 126 on the second plate 120. As will be explained in further detail later, the non-alignment allows for the implant including the keels to be properly positioned between the vertebrae in such a way to accommodate the position of the nerves as the nerves extend out from the between adjacent vertebrae. Additionally, the length of ball 134 from the third end wall 144 to the fourth end wall 146 is shorter than the length of the socket 136 from the end wall 154 to the open end 156 as discussed before.

Figure 3B:
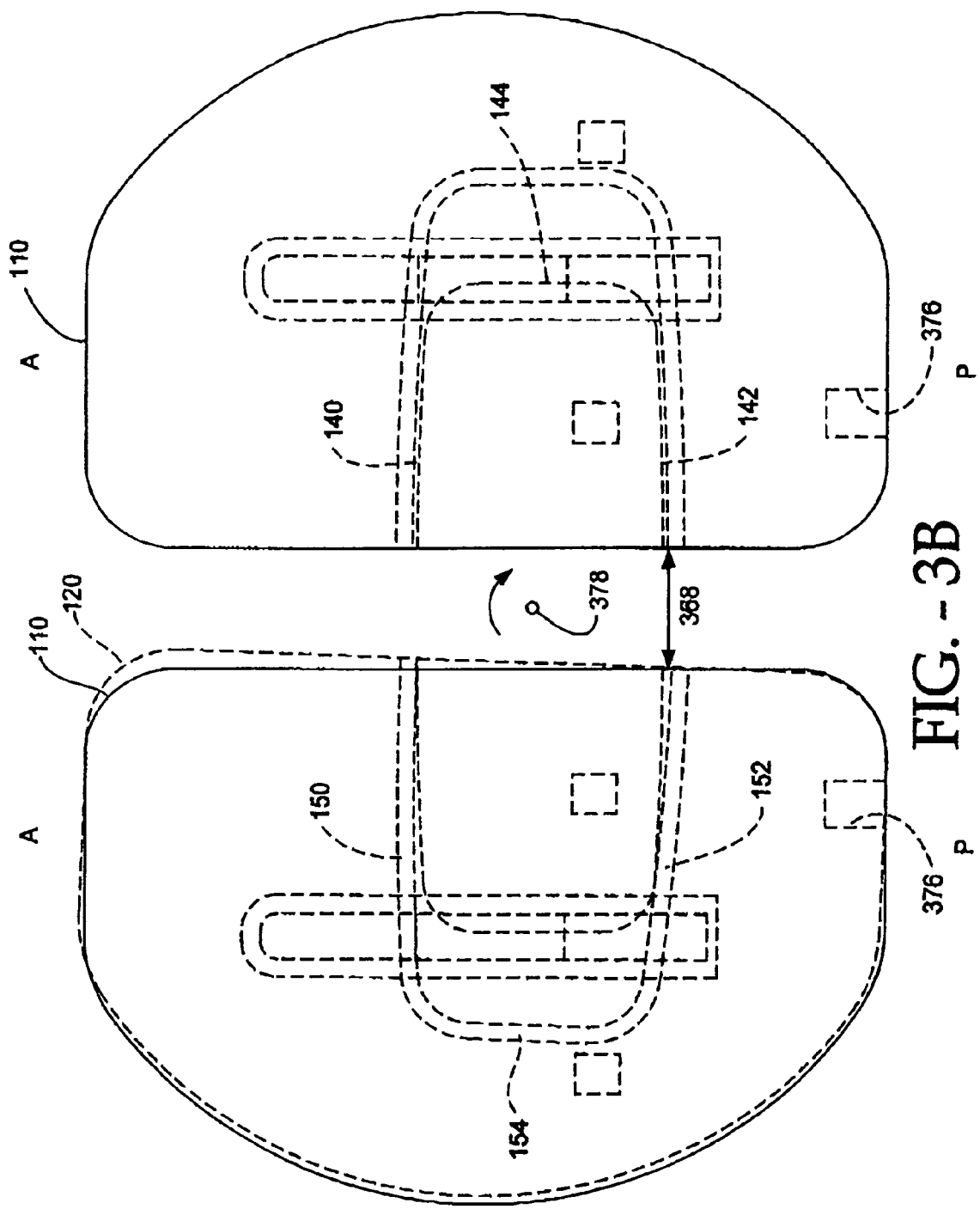
FIG. 3B is a top view of an embodiment of the implant of the invention showing a rotation to the right.
Figure 3C:
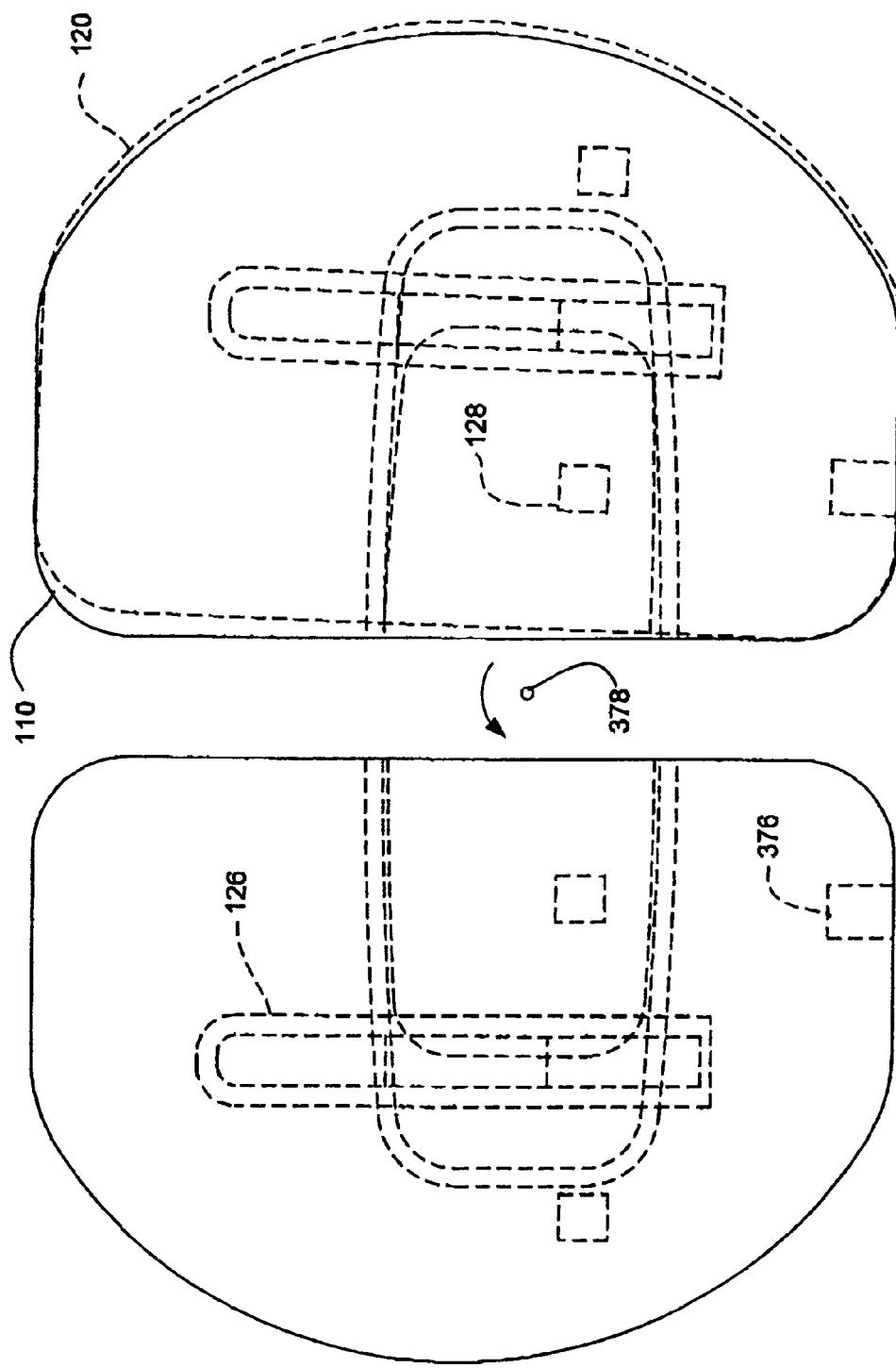
FIG. 3C is a top view of an embodiment of the implant of the invention showing a rotation to the left.

FIGS. 3B and 3C show the relative rotation of the upper first plate 110 to the lower second plate 120 to achieve rotation about a central axis 378. This rotation results in about a 3°–6° rotation about the axis (i.e., 3° of torso twisting in each direction).

Figure 4A:
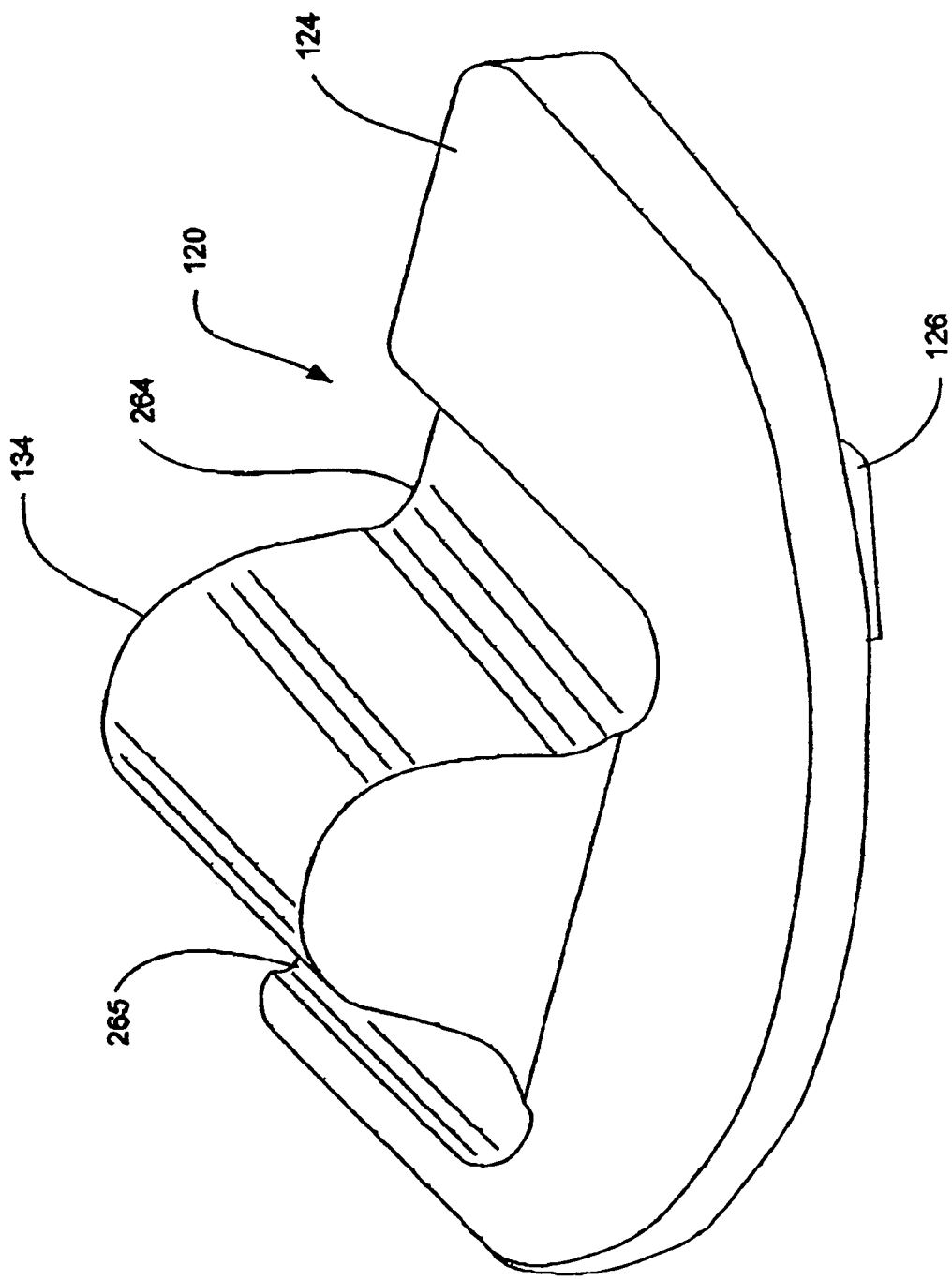
FIG. 4A is a perspective view of a ball portion of the embodiment of the implant of the invention.

FIG. 4A shows a perspective view of a second plate 120 of the intervertebral implant 100. The second surface 124 of the second plate 120 with the ball 134 and channels or grooves 264, 265 extending thereabout. As illustrated in FIG. 4A, the channels 264, 265 are formed on two sides of the ball 134. However, as will be appreciated by those of skill in the art, the channels 264, 265 can alternatively surround the ball 134.

FIG. 4B shows a perspective view of the first plate 110. The first plate 110 has a second surface 114, as described above, and, extending therefrom is the socket 136 therein. The socket 136 of FIG. 4B is configured to mate with the ball 134 of FIG. 4A, as described above.

Figure 5A:
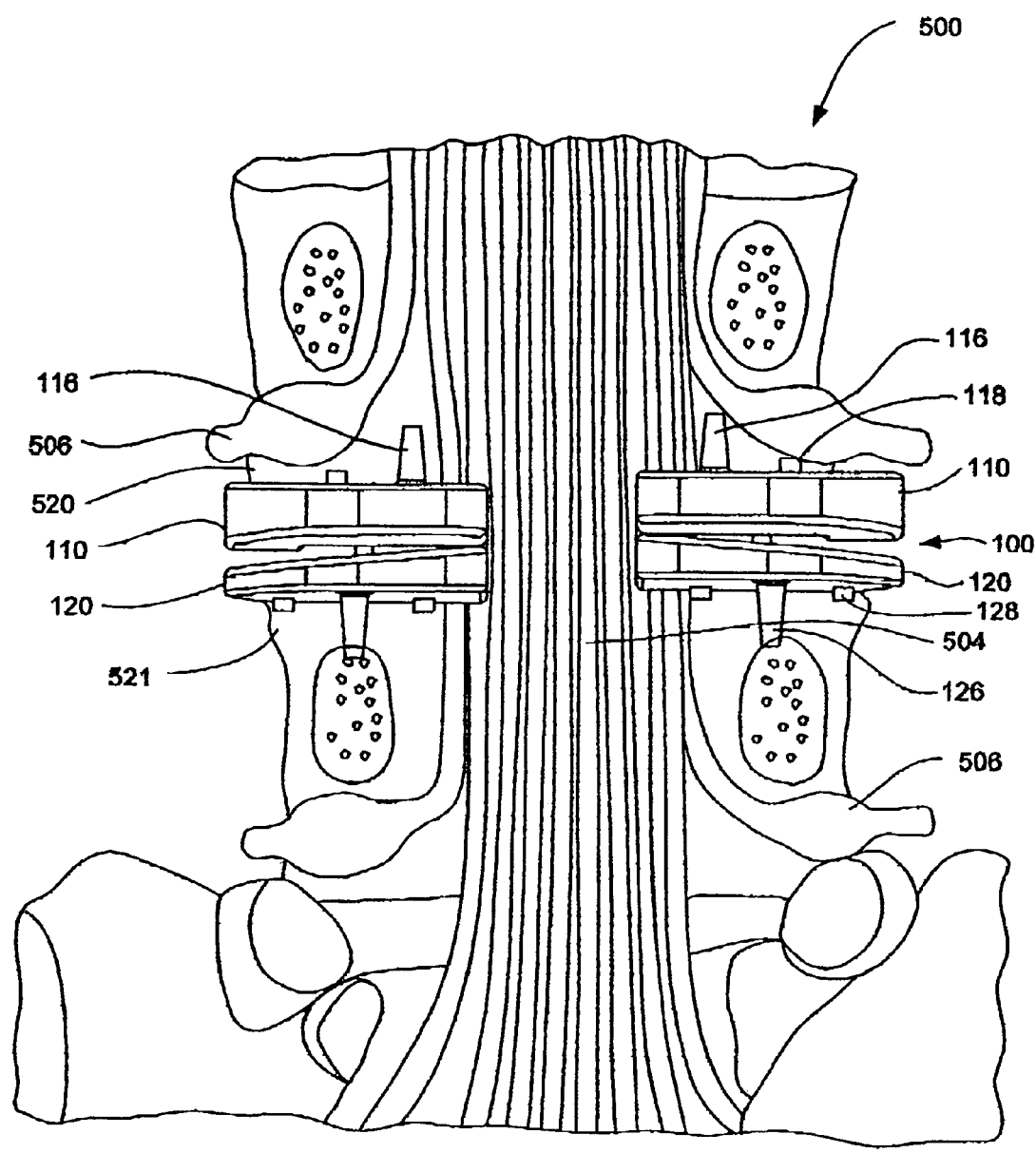
FIG. 5A is a posterior view of the embodiment of the implant of the invention after being implanted between two vertebral bodies.

FIG. 5A illustrates a posterior view of the implant shown in FIG. 1A implanted between vertebral bodies in a spine. FIG. 5A illustrates the spinal column 500 and the cauda equina 504 (a collection of lumbar and sacral nerve roots that fill the caudal end of the spinal cord) with individual nerves 506 exiting the cord between lumbar vertebrae. The implant 100 is positioned between two vertebral bodies 520, 521 such that the keels 116, 126 do not interfere with the cauda equina 504 and the exiting nerve 506. As can be seen in FIG. 5A, the keel 116 of the upper first plates 110 are close together and inboard of the keel 126 of the lower second plate 120. This allows the lower keels 126 to be clear of the nerves 506 as the nerves exit from between the adjacent vertebrae.

Figure 5B:
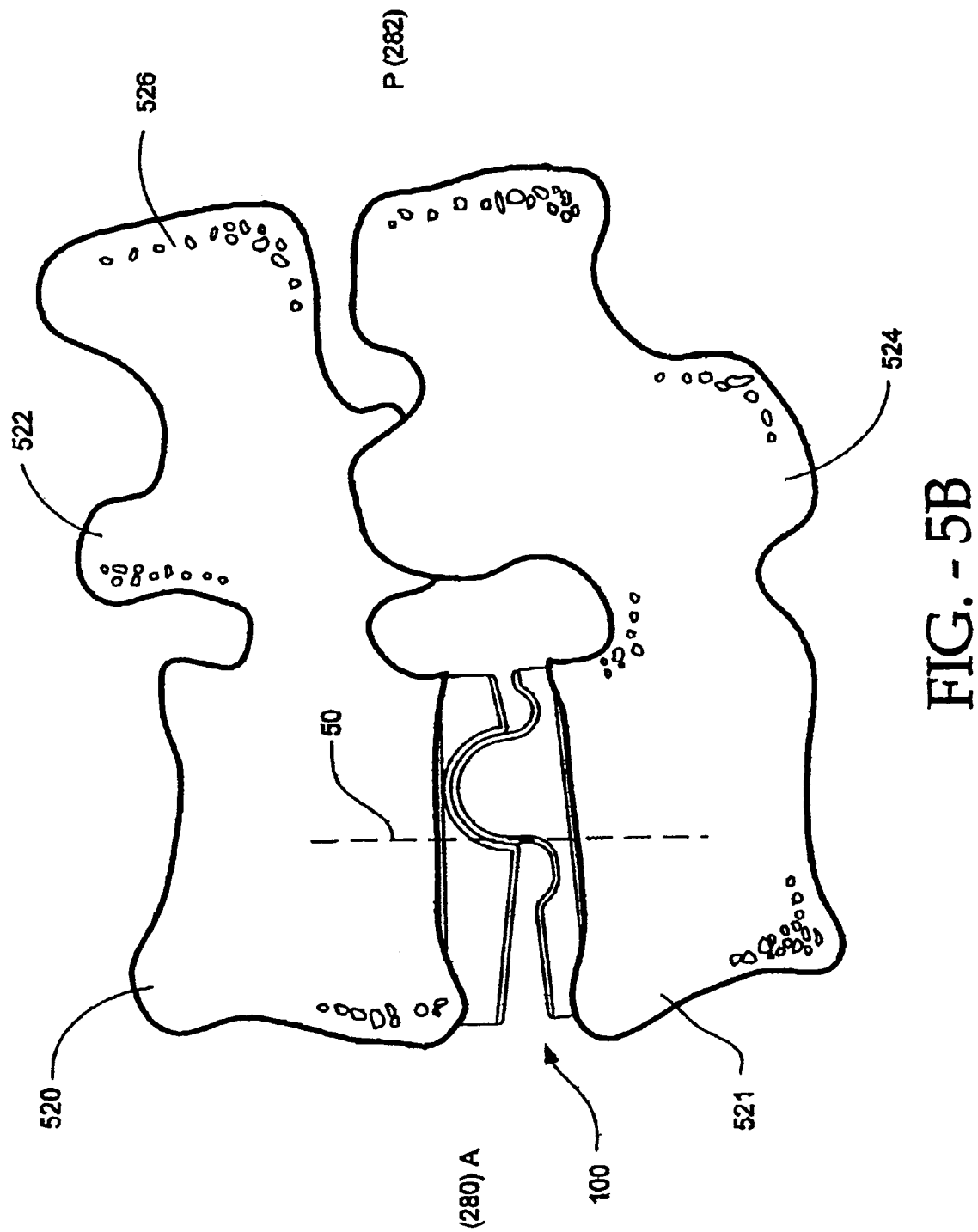
FIG. 5B is a side view of the embodiment of the implant of the invention after being implanted between two vertebral bodies.

FIG. 5B illustrates a side view of the implant 100, such as that shown in FIG. 1A, implanted between vertebral bodies 520, 521. The implant 100 is implanted so that the ball-and-socket joint enables about a 5° extension (backward bending) and about a 10° flexion (forward bending). In this view, the ball and socket arrangement crosses the centerline 50 of the implant 100 and extends in a posterior 282 direction. In this embodiment, the ball-and-socket arrangement can be more centered on the centerline 50 or extend from a position when the implant 100 crosses the centerline 50 and extends in an anterior 280 direction. Further, in another preferred embodiment, the ball can be approximately bisected by the centerline.

Figure 6:
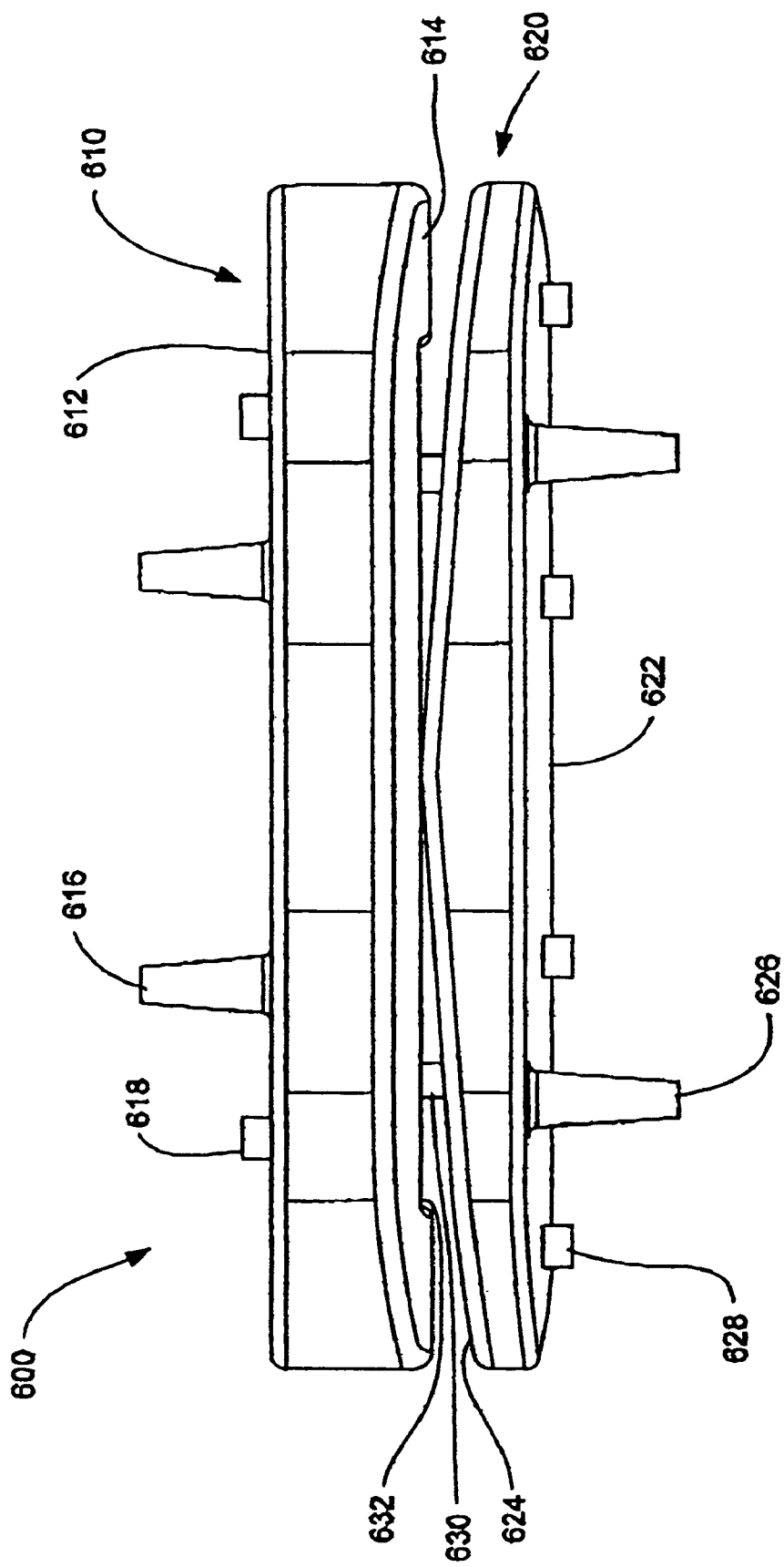
FIG. 6 is a rear view of an alternate embodiment of the invention having two plates.

FIG. 6 illustrates a rear view of an alternate embodiment of the implant shown in FIG. 1A. The implant 600 of FIG. 6 is in the form of a two-piece implant 600 having a first plate 610 and a second plate 620. The first plate 610 has a first surface 612 that contacts the vertebral body and has one or more keels 616 and detents 618 for anchoring the first plate 610 into the vertebral body. The implant 600 also has a second plate 620 that has a first surface 622 that contacts the vertebral body and has one or more keels 626 and detents 628 for anchoring the second plate 620 into the vertebral body. The second surface 614 of the first plate 610 has a socket 632 formed therein while the second surface 624 of the second plate 620 has a ball 630. This implant 600 moves in much the same way as implant 100 described above.

As will be appreciated by those of skill in the art, implant 100 is predominantly designed for a posterior implantation method. However, implant 100 can also be implanted from an anterior direction. Implant 600 is designed for predominantly an anterior implantation approach.

Further, a combination of the two embodiments shown in FIG. 1A and FIG. 6 can be used to create a three-piece implant as will also be appreciated by those of skill in the art. For example, the first plate 610 of FIG. 6 with its socket 632 can be combined with two-second plates 120 of FIG. 1A to form an implant. Similarly, the second plate 620 of FIG. 6 and its ball 630 can be combined with two first plates 110 from FIG. 1A to achieve an implant. Neither of these configurations depart from the scope of the invention. It is also to be understood that the implant 100, 600 can be comprised of any suitable biocompatible material, such as titanium.

Figure 7A:
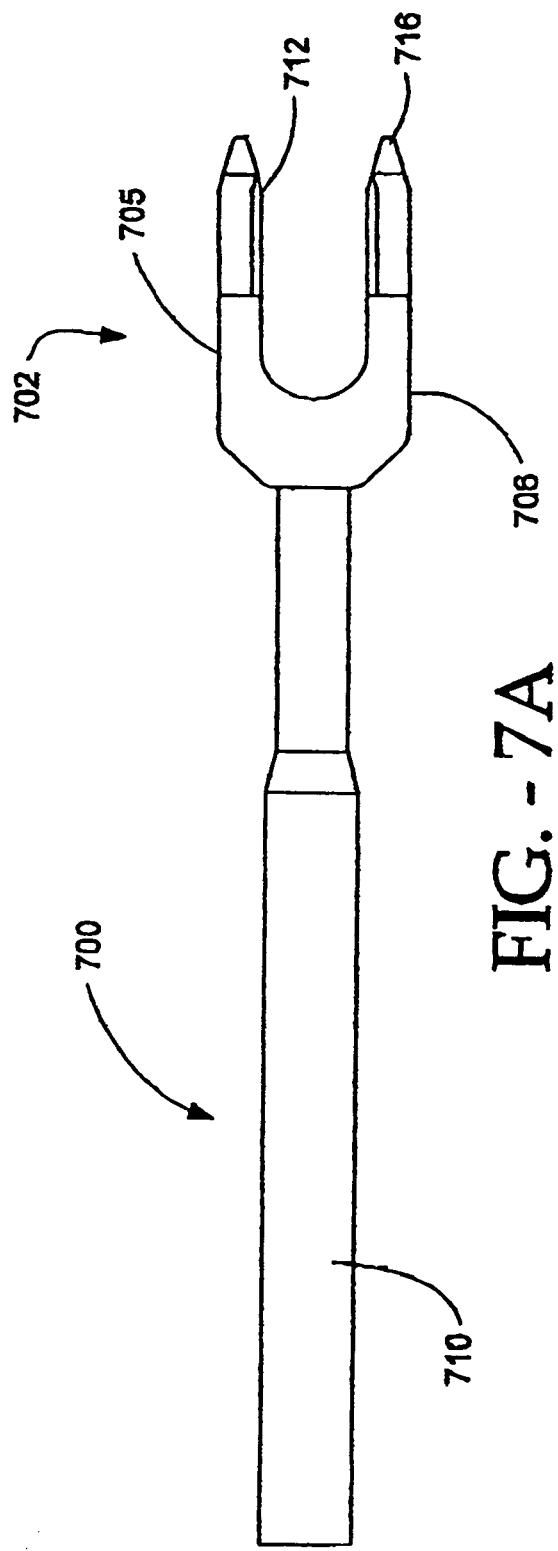
FIG. 7A is a top view of an embodiment of a cutting tool of the invention used to prepare the vertebral bodies for the implant.
Figure 7B:
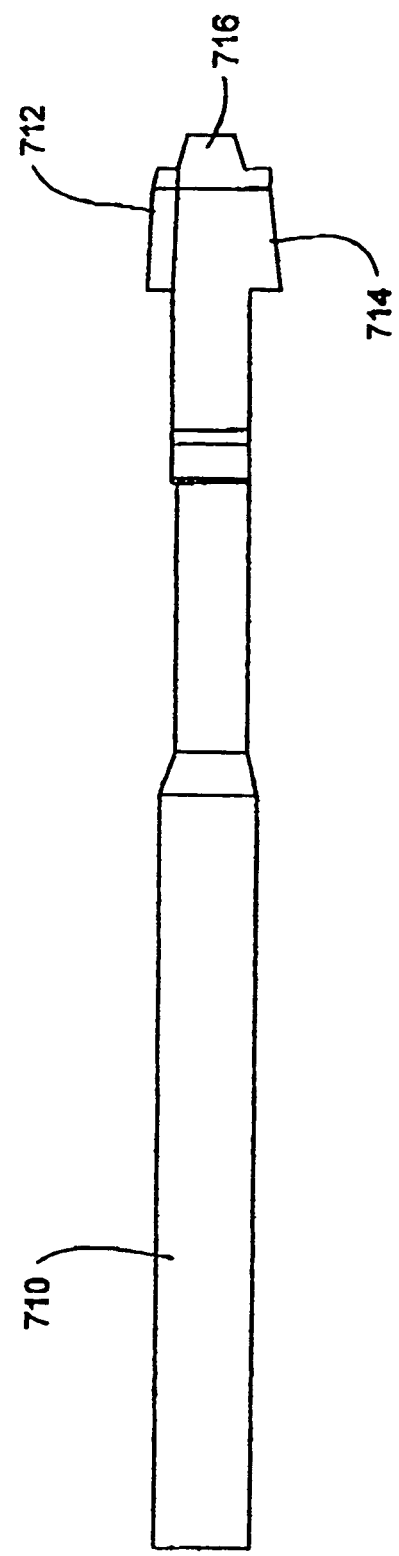
FIG. 7B is a side view of the embodiment of the cutting tool of the invention from the distal end.
Figure 7C:
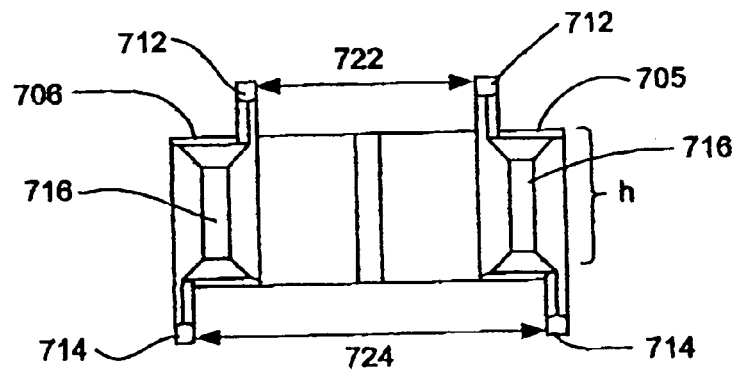
FIG. 7C is a distal end view of an embodiment of the cutting tool of the invention.
Figures 7D, 7E:
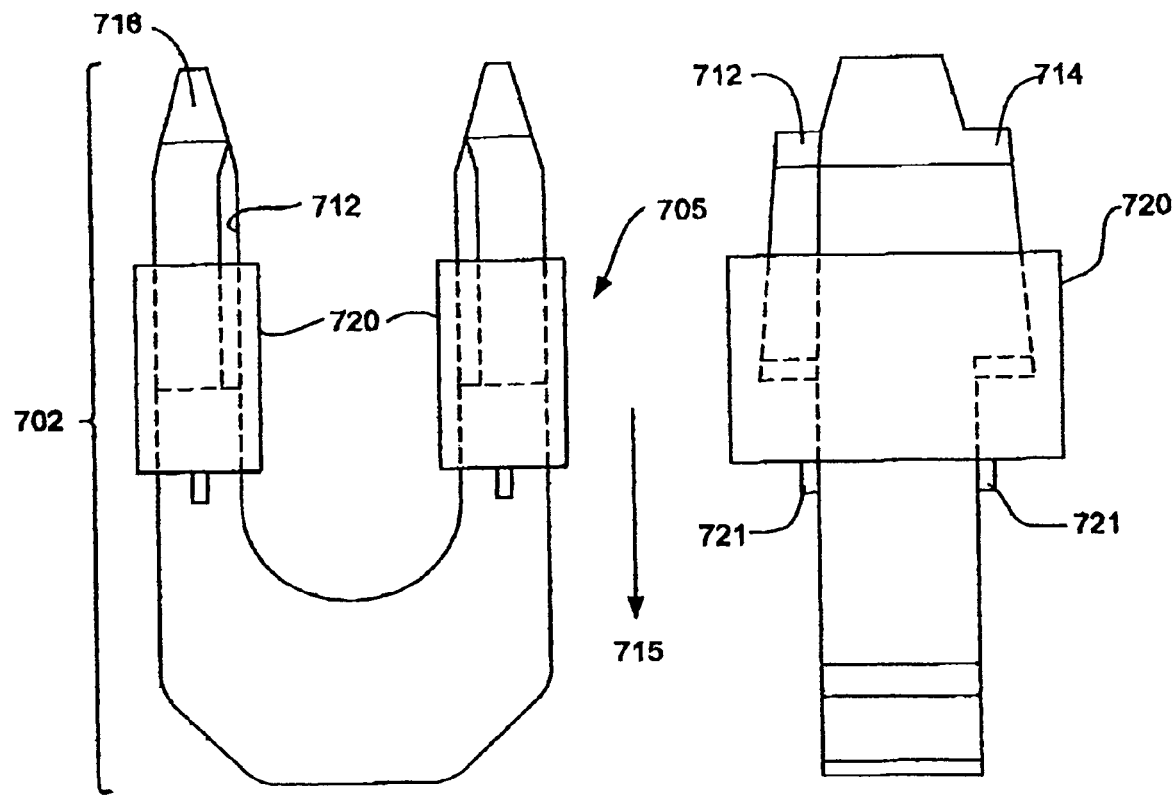
FIG. 7D is a top view of the cutting portion of an alternative embodiment of the cutting tool of the invention showing blade protectors.
FIG. 7E is a side view of the cutting portion of an alternative embodiment of the cutting tool of the invention showing the blade protectors.
Figure 8C:
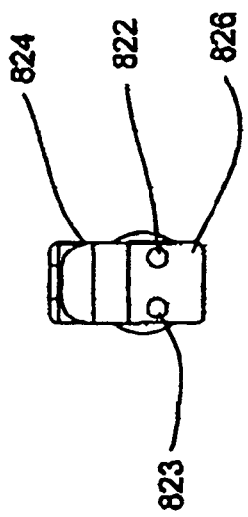
FIG. 8C is a distal end view of the embodiment of the implant insertion tool of the invention.
Figure 8D:
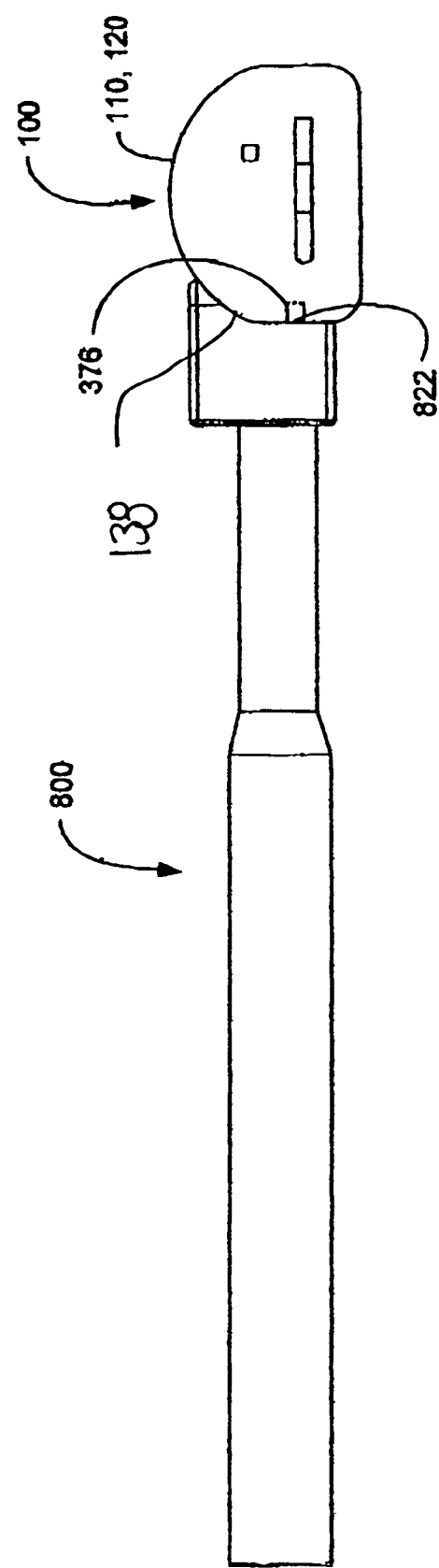
FIG. 8D is a top view of an embodiment of the implant insertion tool holding an embodiment of the implant.

Turning now to FIGS. 7 and 8 and the tools for preparing the vertebral bodies and implanting the implant 100 as described. FIG. 7A depicts a top view of a cutting tool 700 used to prepare the vertebral bodies for the implant 100 and FIG. 7B depicts a side view of tool 700. The cutting tool 700 has a handle 710 at its proximal end for controlling the tool during operation. As will be appreciated by those of skill in the art, the handle 710 can be removable or affixed to the cutting end.

The distal end 702 of the tool 700 is forked to form two prongs or tines 705, 706. The end of each tine 705, 706 has a beveled edge 716 at its distal most end. Each tine 705, 706 also has an inner blade 712 located on an inner upper side and an outer blade 714 located on an outer lower side (shown in FIG. 7C). Preferably the inner blades 712 are coplanar with the surface of the inner side of the tine and the outer blades 714 are coplanar with the outer side of the tine. The inner blades 712 are oriented to cut a space in a first intervertebral body for the first surface keel 116 of the implant and the outer blades 714 are oriented to cut a space in the facing intervertebral body for the second surface keel 126. The orientation of the blades is such that each of the cuts made for the keels of the implant are offset and avoid the nerves in the cauda equina or exiting the cauda equina.

FIG. 7C is a view of the distal end of the cutting tool 700 showing the beveled edges 716 of the tines 705, 706 and the inner blades 712 and outer blades 714. The distance 722 between the inner blades 712 is less than the distance 724 between the outer blades and the height h of the tines approximates the distance between two vertebral bodies or the height of the disk space. The blades 712, 714 extend above and below the tines or the height of the tines. As can be seen in FIG. 7C, the beveled sides of the distal end 716 extend and form at least one of the beveled sides of the blades 712, 714.

FIG. 7D depicts an enlarged top view of the tines 705, 706 of the distal end of cutting tool 700 with the beveled distal edges 716. FIG. 7E is an enlarged side view of the distal end of cutting tool 700. FIGS. 7D and 7E show the retractable blade protector 720 for the blade 712 positioned in a retracted position. As the cutting tool is inserted between vertebral bodies, the retractable blade protector 720 moves in a posterior direction 715 (i.e., toward the handle 710) to expose the inner blade 712 and the outer blade 714 and to enable the blades to cut into the vertebral bodies. These protectors 720 can be spring biased as desired in order to cover the blade 712, 714 as the tool 700 is inserted past the nerves. The protectors 720 are urged in a posterior direction as the blades 712, 714 are urged into the vertebral bodies in order to cut channels for the keels. Springs 721 provide the desired bias to keep the protectors 720 in a forward position covering the blades 712, 718.

As will be appreciated by those of skill in the art, the tool shown in FIG. 7 can be modified such that instead of cutting keel-receiving channels in the upper and lower vertebral bodies at the same time, two tools are provided so that only one vertebral body is cut for keel-receiving channels at a time. For example, a first tool having two tines as described above could be provided having a pair of inner blades located on an upper surface of the tines. A second tool could be provided having tines as described with a pair of outer blades located on the lower surface of the tines. Optionally, the second tool can have a guide corresponding to the location of the first blade on the first tool to ensure that the second cut is optimally aligned with the first cut. In use, a pair of channels can be cut into the upper vertebral body using the first tool. Thereafter a second pair of channels can be cut into the lower vertebral body. Alternate arrangements are also possible, for example, where the first tool has a pair of outer blades and the second tool has a pair of inner blades, or where the first tool has upper and lower blades on a first tine (e.g., right tine) and the second tool has upper and lower blades on a second tine (e.g., left tine).

FIG. 8A depicts the implanting tool used to insert the implant 100 of FIG. 1A between vertebral bodies. FIG. 8A is a side view of the implantation tool 800 that has a handle 810 and an implant holder 820. The implant holder 820 has an implant conforming surface 824 and two pins 822 for holding a first plate 110 and a second plate 120 of a first half of the implant 100. The conforming surface 824 is curved to follow the convex outer edges 138, 139 of the plate 100, 120, respectively (shown in FIG. 3A). The implant 100 nests within a conforming surface 824 and is held by pins 822. FIG. 8C shows the distal view of the end of the tool with two pins 822, 823 for securing the first and second plate of the implant. The tool can be rotated by the user 180° to implant the other half of the implant.

Where an implant such as that shown in FIG. 6 is implanted, the implant conforming surface 824 of the implant tool would have a mirror image conforming surface provided to capture the implant 600. An additional series of pins, for a total of four, can be provided for holding a first plate 610 and a second plate 620 of the implant 600, if required. The implant 600 would nest within the conforming surface of the "U" shaped cavity.

A variety of kits can be assembled that include an implant 100 (or 600) sized for a particular patient. The kit could also include several cutting tools 700 and several implanting tools 800 or a single handle that cooperates with cutting ends 702 and implantation ends 820.

Figure 9:
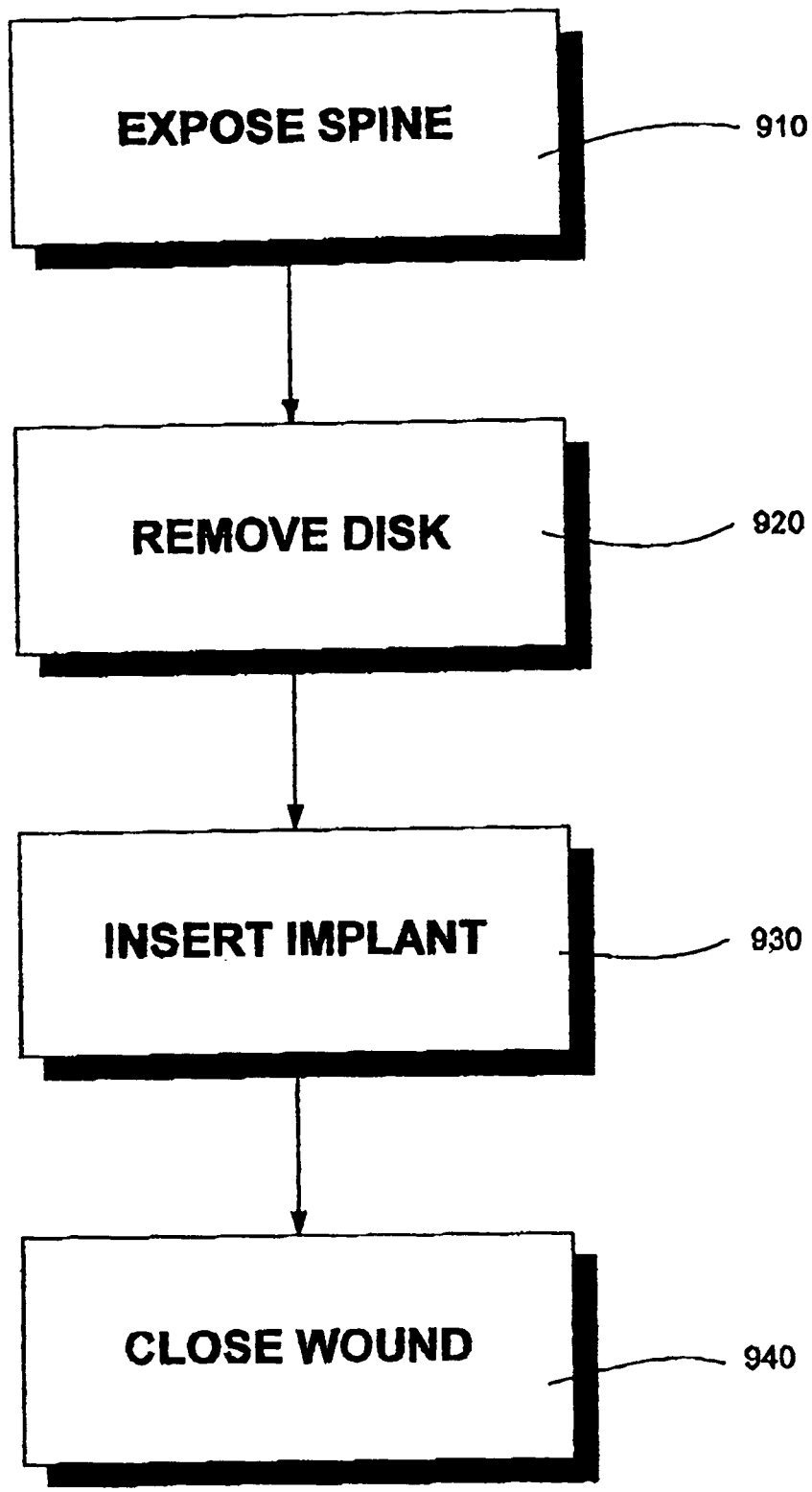
FIG. 9 is a block diagram illustrating the steps of a method for inserting the implant between vertebral bodies.

FIG. 9 is a block diagram showing the steps for implanting an implant. In order to implant the implant of FIG. 1A, the spine is exposed posteriorly 910. The intervertebral disk to be replaced is either partially or completely removed 920. The cutting tool 700 is inserted between the vertebral bodies to create channels in the bodies to receive the keels of the implant. Nerves can be retracted and then the implant holder 810 is used to insert the implant between the vertebral bodies 930, lining the keels up with the channels created by the cutting tool 700. Next, the nerves are retracted in the other direction and the other plates 100, 120 are attached to a tool and are implanted. The implant first and second plates 110, 120 are now inserted between the vertebrae, and the keel are placed in the channels prepared by the cutting tool 700. Once the implant is inserted, the wound is closed 940.

In order to implant the implant of FIG. 6, the spine is exposed anteriorly 910. The intervertebral disk to be replaced is either partially or completely removed 920. The cutting tool 700 is inserted between the vertebral bodies to create channels in the bodies to receive the keels of the implant. The implant is then inserted into an implant holder and the implant tool is used to insert the implant between the vertebral bodies 930, lining the keels up with the channels created by the cutting tool 700. Once the implant is inserted, the wound is closed 940.

The foregoing description of embodiments of the present invention has been provided for the purposes of illustration and description. It is not intended to be exhaustive or to limit the invention to the precise forms disclosed. Many modifications and variations will be apparent to the practitioner skilled in the art. The embodiments were chosen and described in order to best explain the principles of the invention and its practical application, thereby enabling others skilled in the art to understand the invention and the various embodiments and with various modifications that are suited to the particular use contemplated. It is intended that the scope of the invention be defined by the following claims and their equivalence.

What is claimed:

1. An intervertebral implant comprising:
   a first plate adapted to mate to a first vertebral body, the first plate including an elongated socket;
   a second plate adapted to mate to a second vertebral body, the second plate including an elongated ball, with the elongated ball having a top surface and first and second elongated sidewalls that are substantially perpendicular to the second plate, and third and fourth end walls; and
   the top surface slopes from the third end wall to the fourth end wall wherein the third end wall has a height greater than a height of the fourth end wall.

2. The implant of claim 1 including at least one of the first and second plates including a keel extending there from and adapted to engage a vertebral body.

3. The implant of claim 1 including a first keel extending from the first plate and adapted to engage a first vertebral body, and a second keel extending from the second plate and adapted to engage a second vertebral body.

4. The implant of claim 1 including a first keel extending from the first plate and substantially perpendicular to the elongated socket and adapted to engage a first vertebral body, and a second keel extending from the second plate and substantially perpendicular to the elongated ball and adapted to engage a second vertebral body.

5. The implant of claim 1 wherein the elongated socket has first and second sidewalk that are substantially perpendicular to the first plate.

6. The implant of claim 1 wherein the third end wall and the fourth end wall are substantially perpendicular to the second plate.

7. The implant of claim 1 including at least one of the first and second plates including a keel extending therefrom and adapted to engage a vertebral body.

8. An intervertebral implant comprising:
   a first plate adapted to mate to a first vertebral body, the first plate including an elongated socket;
   a second plate adapted to mate to a second vertebral body, the second plate including an elongated ball, with the elongated ball having a top surface and first and second elongated sidewalls that are substantially perpendicular to the second plate, and third and fourth end walls; and
   the top surface slopes downward from the third end wall to the fourth end wall wherein the socket has first and second elongated sidewalls, an end wall, and an open end.

9. An intervertebral implant comprising:
   a first plate adapted to mate to a first vertebral body, the first plate including an elongated socket;
   a second plate adapted to mate to a second vertebral body, the second plate including an elongated ball, with the elongated ball having a top surface and first and second elongated sidewalls, and third and fourth end walls; and
   the top surface slopes from the third end wall to the fourth end wall, wherein the third end wall has a height that is greater than a height of the fourth end wall.

10. The implant of claim 9 including a first keel extending from the first plate and adapted to engage a fist vertebral body, and a second keel extending from the second plate and adapted to engage a second vertebral body.

11. The implant of claim 9 including a first keel extending from the first plate and substantially perpendicular to the elongated socket and adapted to engage a first vertebral body, and a second keel extending from the second plate and substantially perpendicular to the elongated ball and adapted to engage a second vertebral body.

12. The implant of claim 9 wherein the socket has first and second elongated sidewalls that are substantially perpendicular to the first plate.

13. The implant of claim 9 wherein the third end wall and the fourth end wall are substantially perpendicular to the second plate.

14. An intervertebral implant comprising:
   a first plate adapted to mate to a first vertebral body, the first plate including an elongated socket;
   a second plate adapted to mate to a second vertebral body, the second plate including an elongated ball, with the elongated ball having a top surface and first and second elongated sidewalls, and third and fourth end walls; and
   the top surface slopes downward from the third end wall to the fourth end wall, the socket has first and second elongated sidewalls, an end wall, and an open end.

15. An intervertebral implant comprising:
   a pair of first plates adapted to mate to a first vertebral body, and each of the first plates including an elongated socket;
   a pair of second plates adapted to mate to a second vertebral body, each of the second plates including an elongated ball, with the elongated ball of each the second plates having a top surface and first and second elongated sidewalls that are substantially perpendicular to the respective second plates, and each the elongated ball having third and fourth end walls; and
   the top surface of each the elongated ball slopes from the third end wall to the fourth end wall wherein each third end wall has a height that is greater than a height of each fourth end wall.

16. The implant of claim 15 including at least one of the pair of first plates and the pair of second plates including a keel extending from each plate and which keel is adapted to engage a vertebral body.

17. The implant of claim 15 including a first keel extending firm each plate of the pair of first plates and adapted to engage a first vertebral body, and a second keel extending from each plate of the pair of second plates and adapted to engage a second vertebral body.

18. The implant of claim 15 including a first keel extending from each plate of the pair of first plates and substantially perpendicular to the elongated socket and adapted to engage a first vertebral body, and a second keel extending from each plate of the pair of second plates and substantially perpendicular to the elongated ball and adapted to engage a second vertebral body.

19. The implant of claim 15 wherein the first and second sidewalls of the elongated socket are substantially perpendicular to the first plate.

20. The implant of claim 15 wherein the third end wall and the fourth end wall are substantially perpendicular to the second plate.

21. The implant of claim 15 wherein the third end walls of each of the elongated balls are adjacent each other.

22. An intervertebral implant comprising:
   a pair of first plates adapted to mate to a first vertebral body, and each of the first plates including an elongated socket;
   a pair of second plates adapted to mate to a second vertebral body, each of the second plates including an elongated ball, wit the elongated ball of each the second plates having a top surface and first and second elongated sidewalls that are substantially perpendicular to the respective second plates, and each the elongated ball having third and fourth end walls; and the top surface of each the elongated ball slopes downward from the third endwall to the fourth end wall, each elongated socket has first and second elongated sidewalls, an end wall, and an open end.

23. The implant of claim 22 wherein the third end walls of each of the elongated balls are adjacent each other.

24. An intervertebral implant comprising:
a pair of first plates adapted to mate to a first vertebral body, and each of the first plates including an elongated socket;
a pair of second plates adapted to mate to a second vertebral body, the each of the second plates including an elongated ball, with the elongated ball of each the second plates having a top surface and first and second elongated sidewalls, and each the elongated ball having third and fourth end walls, each third end wall has a height that is greater than a height of each fourth end wall; and
the top surface of each the elongated ball slopes from the third end wall to the fourth end wall.

25. The implant of claim 24 including at least one of the pair of first plates and the pair of second plates including a keel extending from each plate and which keel is adapted to engage a vertebral body.

26. The implant of claim 24 including a first keel extending from each plate of the pair of first plates and adapted to engage a first vertebral body, and a second keel extending from each plate of the pair of second plates and adapted to engage a second vertebral body.

27. The implant of claim 24 including a first keel extending from each plate of the pair of first plates and substantially perpendicular to the elongated socket and adapted to engage a first vertebral body, and a second keel extending from each plate of the pair of second plates and substantially perpendicular to the elongated ball and adapted to engage a second vertebral body.

28. The implant of claim 24 wherein the first and second sidewalls of the elongated socket are substantially perpendicular to the first plate.

29. The implant of claim 24 wherein the third end wall and the fourth end wall are substantially perpendicular to the second plate.

30. The implant of claim 24 wherein the third end walls of each of the elongated balls are adjacent each other.

31. An intervertebral implant comprising:
a pair of first plates adapted to mate to a first vertebral body, and each of the first plates including an elongated socket;
a pair of second plates adapted to mate to a second vertebral body, the each of the second plates including an elongated ball, with the elongated ball of each the second plates having atop surface and first and second elongated sidewalls, and each the elongated ball having third and fourth end walls; and
the top surface of each the elongated ball slopes downward from the third end wall to the fourth end wall,
wherein each elongated socket has first and second elongated sidewalls, an end wall, and an open end.

32. The implant of claim 31 wherein the third end walls of each of the elongated balls are adjacent each other.

33. An intervertebral implant comprising:
a first plate having an elongated socket formed thereon; and
a second plate having a ball formed thereon, wherein the ball has first and second sidewalls that are substantially perpendicular to a surface of the second plate,
wherein the first plate has a protuberance adjacent the socket, and
wherein the protuberance is adjacent the socket on three sides.

34. An intervertebral implant comprising:
a first plate having a socket formed thereon; and
a second plate having a ball formed thereon,
wherein the ball has a top that slopes downward from a first side to a second side and sidewalls perpendicular to a surface of the second plate,
wherein the first plate has a keel, and wherein the keel has teeth.

35. An intervertebral implant comprising:
a first plate having a socket formed thereon; and
a second plate having a ball formed thereon,
wherein the ball has a top that slopes downward from a first side to a second side and sidewalls perpendicular to a surface of the second plate,
wherein the second plate has a keel, and
wherein the keel has teeth.

* * * * *

UNITED STATES PATENT AND TRADEMARK OFFICE
CERTIFICATE OF CORRECTION

| | | |
|---|---|---|
| PATENT NO. | : 7,083,649 B2 | |
| APPLICATION NO. | : 10/684669 | |
| DATED | : August 1, 2006 | |
| INVENTOR(S) | : Zucherman et al. | |

It is certified that error appears in the above-identified patent and that said Letters Patent is hereby corrected as shown below:

Column 9,
Line 34, delete "sidewalk" and insert therefore -- sidewalls --.

Column 9,
Line 65, delete "fist" and insert therefore -- first --.

Column 11,
Line 1, delete "wit" and insert therefore -- with --.

Column 11,
Line 7, delete "endwall" and insert therefore -- end wall --.

Column 12,
Line 10, delete "atop" and insert therefore -- a top --.

Signed and Sealed this

Twenty-eighth Day of November, 2006

JON W. DUDAS
*Director of the United States Patent and Trademark Office*